(12) United States Patent
Benner

(10) Patent No.: US 9,666,423 B2
(45) Date of Patent: May 30, 2017

(54) INSTRUMENTS FOR MEASURING ION SIZE DISTRIBUTION AND CONCENTRATION

(71) Applicant: W Henry Benner, Danville, CA (US)

(72) Inventor: W Henry Benner, Danville, CA (US)

(*) Notice: Subject to any disclaimer, the term of this patent is extended or adjusted under 35 U.S.C. 154(b) by 0 days.

(21) Appl. No.: 14/718,948

(22) Filed: May 21, 2015

(65) Prior Publication Data

US 2015/0340221 A1 Nov. 26, 2015

Related U.S. Application Data

(60) Provisional application No. 62/002,128, filed on May 22, 2014.

(51) Int. Cl.
*H01J 49/22* (2006.01)
*H01J 49/10* (2006.01)
*H01J 49/04* (2006.01)
*G01N 27/62* (2006.01)
*H01J 49/16* (2006.01)

(52) U.S. Cl.
CPC ............ *H01J 49/22* (2013.01); *G01N 27/622* (2013.01); *H01J 49/0445* (2013.01); *H01J 49/10* (2013.01); *H01J 49/167* (2013.01)

(58) Field of Classification Search
USPC .................................................. 250/288, 282
See application file for complete search history.

(56) References Cited

U.S. PATENT DOCUMENTS

| 4,542,293 | A | * | 9/1985 | Fenn .................... B01D 59/44 250/288 |
| 4,777,363 | A | | 10/1988 | Eiceman et al. |
| 5,352,892 | A | * | 10/1994 | Mordehai ............ G01N 30/7266 250/288 |
| 5,637,869 | A | | 6/1997 | Bergmann |
| 5,719,392 | A | | 2/1998 | Franzen et al. |
| 5,747,799 | A | | 5/1998 | Franzen |
| 5,905,258 | A | | 5/1999 | Clemmer et al. |
| 5,936,242 | A | | 8/1999 | De La Mora et al. |
| 6,051,832 | A | | 4/2000 | Bradshaw |
| 6,107,628 | A | | 8/2000 | Smith et al. |
| 6,229,142 | B1 | | 5/2001 | Bateman et al. |

(Continued)

FOREIGN PATENT DOCUMENTS

GB 2463149 3/2013

OTHER PUBLICATIONS

Bacher et al., Charge-reduced nano electroscopy ionization combined with differential mobility analysis of peptides, proteins, glycoproteins, noncovalent protein complexes and viruses, Journal of Mass Spectrometry, 2001, 36, 1038-1052, 36, John Wiley & Sons, Ltd.

(Continued)

*Primary Examiner* — Phillip A Johnston
(74) *Attorney, Agent, or Firm* — John P. Wooldridge

(57) ABSTRACT

Instruments are disclosed for analyzing ions from about 1000 to 10,000,000 Daltons by controlling a gaseous medium through which the ions travel under the influence of an electric field so that properties of the ions, such as diameter, electrical mobility, and charge, are measured. One embodiment of the disclosed instruments include an ion source, a nozzle, a jet relaxation region, an ion accumulation region, an electronic gate, a flow chamber and an ion detector.

25 Claims, 37 Drawing Sheets

(56) References Cited

U.S. PATENT DOCUMENTS

| | | | |
|---|---|---|---|
| 6,230,572 B1 | 5/2001 | Pui et al. | |
| 6,323,482 B1 | 11/2001 | Clemmer et al. | |
| 6,498,342 B1 | 12/2002 | Clemmer | |
| 6,583,407 B1 | 6/2003 | Fischer et al. | |
| 6,586,732 B2 | 7/2003 | Lee et al. | |
| 6,593,567 B1 | 7/2003 | Abdel-Rahman | |
| 6,768,108 B2* | 7/2004 | Hirano | H01J 49/105 250/288 |
| 6,818,890 B1 | 11/2004 | Smith et al. | |
| 6,967,325 B2 | 11/2005 | Smith et al. | |
| 6,969,349 B1 | 11/2005 | Spence et al. | |
| 7,164,122 B2 | 1/2007 | Fuhrer et al. | |
| 7,244,931 B2 | 7/2007 | Zimmermann et al. | |
| 7,268,347 B1 | 9/2007 | Blanchard | |
| 7,351,964 B2 | 4/2008 | Tolmachev et al. | |
| 7,495,212 B2 | 2/2009 | Kim et al. | |
| 7,514,676 B1 | 4/2009 | Page et al. | |
| 7,541,576 B2 | 6/2009 | Belov et al. | |
| 7,671,344 B2 | 3/2010 | Tang et al. | |
| 7,888,635 B2 | 2/2011 | Belov et al. | |
| 8,173,960 B2 | 5/2012 | Tang et al. | |
| 8,217,372 B2* | 7/2012 | Harrison | H01J 37/08 250/281 |
| 8,324,565 B2 | 12/2012 | Mordehai et al. | |
| 8,373,120 B2* | 2/2013 | Verentchikov | H01J 49/062 250/281 |
| 8,541,737 B2 | 9/2013 | Ibrahim et al. | |
| 8,698,075 B2 | 4/2014 | Kurulugama et al. | |
| 8,921,772 B2 | 12/2014 | Verenchikov | |
| 2001/0032930 A1 | 10/2001 | Gillig et al. | |
| 2012/0097845 A1 | 4/2012 | Prosser et al. | |

OTHER PUBLICATIONS

Bagal, et al., Resolving Disulfide Structural Isoforms of IgG2 Monoclonal Antibodies by Ion Mobility Mass Spectrometry, Analytical Chemistry, 2010, vol. 82, No. 16, 6751-6755, American Chemical Society.

Benesch et al., Protein Complexes in the Gas Phase: Technology for Structural Genomics and Proteomics, Chemical Reviews, 2007, vol. 107 (8), 3544-3567, American Chemical Society.

Campuzano at al., Structural Characterization of Drug-like Compounds by Ion Mobility Mass Spectrometry: Comparison of Theoretical and Experimentally Derived Nitrogen Collision Cross Sections, Analytical Chemistry, 2011, 84, 1026-1033, ACS Publications.

Clowers at al., Enhanced Ion Utilization Efficiency Using an Electrodynamic Ion Funnel Trap as an Injection, Mechanism for Ion Mobility Spectrometry, Analytical Chemistry, 2008, vol. 80, No. 3, 612-523, American Chemical Society.

Fernandez-Lima et al., Integration of trapped ion mobility spectrometry with mass spectrometry Review of Scientific Instruments, 2011, 82, 82-84, AIP Publishing.

Freeke et al., Gas-phase protein assemblies, Unfolding landscapes and preserving native-like structures using noncovalent adducts, Chemical Physics Letters, 2011, 524, 1-9, Elsevier.

Gerlich, Molecular Ions and Nanoparticles in RF and AC Traps, Hyperfine Interactions, 2003, vol. 147/147, 293-306, Kluwer Academic Publishers.

Giles et al., Applications of a travelling wave-based radio-frequency only stacked ring ion guide, Rapid Communications in Mass Spectrometry, 2004, 18, 2014-2414, John Wiley & Sons, Ltd.

Hernandez et al., Ion dynamics in a trapped ion mobility spectrometer, Analyst, 2014, 139, 1913-1921, The Royal Society of Chemistry 2014.

Julian et al., Ion Funnels for the Mass Experiments and Simulations with a Simplified Ion Funnel, J Am Soc Mass Spectrom, 2005, 16, 1708-1712, Elsevier Inc.

Kelly et al., The Ion Funnel: Theory, Implementations, and Applications, Mass Spectrometry Reviews, 2009, 29, 294-312, Wiley Periodicals, Inc.

Komermann et al., Mass Spectrometry Methods for Studying for Structure and Dynamics of Biological Macromolecules, Analytical Chemistry, 2014, 86, 213-232, ACS Publications.

Maiber et al., Determination of gas phase protein ion densities via ion mobility analysis with charge reduction, Phys. Chem. Chem. Phys., 2013, 13, 21630-21641, Owner Societies.

Marklund et al., Collision Cross Sections for Structural Proteomics, Structure, 2015, 23, 791-799, Elsevier Ltd.

Pacholarz et al., Dynamics of Intact Immunoglobulin G Explored by Drift-Tube Ion-Mobility Mass Spectrometry and Molecular Modeling, Agnew. Chem. Int. Ed. 2014, 53, 7765-7769, Wiley Online Library.

Pease III et al., Determination of Protein Aggregation with Differential Mobility Analysis: Application to IgG Antibody, Biotechnol. Bioeng. 2008, 101, 1214-1222, Wiley Periodicals, Inc.

Pritchard et al., The Role of Ion Mobility Spectrometry-Mass Spectrometry in the Analysis of Protein Reference Standards, Anal. Chem., 2013, 85, 7205-7212, ACS Publications.

Shi et al., Conformation Types of Ubiquitin [M+8H]8+ Ions from Water:Methanol Solutions: Evidence for the N and A States in Aqueous Solution, J. Phys. Chem. B, 2012, 116, 3344-3352, ACS Publications.

Uetrecht et al., Ion mobility mass spectrometry of proteins and protein assemblies, Chem. Soc. Rev., 2010, 39, 1633-1655, The Royal Society of Chemistry.

Zucker et al., An Ion Mobility/Ion Trap/Photodissociation Instrument for Characterization of Ion Structure, J. Am. Soc. Mass Spectom., 2011, 22, 1477-1485, American Society for Mass Spectrometry.

Hakansson et al., Design and performance of an electrospray ionization time-of-flight mass spectrometer, Review of Scientific Instruments, 2000, 71, 36-41, AIP Publishing.

SIN, Atmospheric Pressure Ionization Time-of-Flight Mass Spectrometry with a Supersonic Ion Beam, Anal. Chem. 1991, 63, 2897-2900, American Chemical Society.

European Patent Office, International Search Report, 2015.
European Patent Office, Written Opinion, 2015.

* cited by examiner

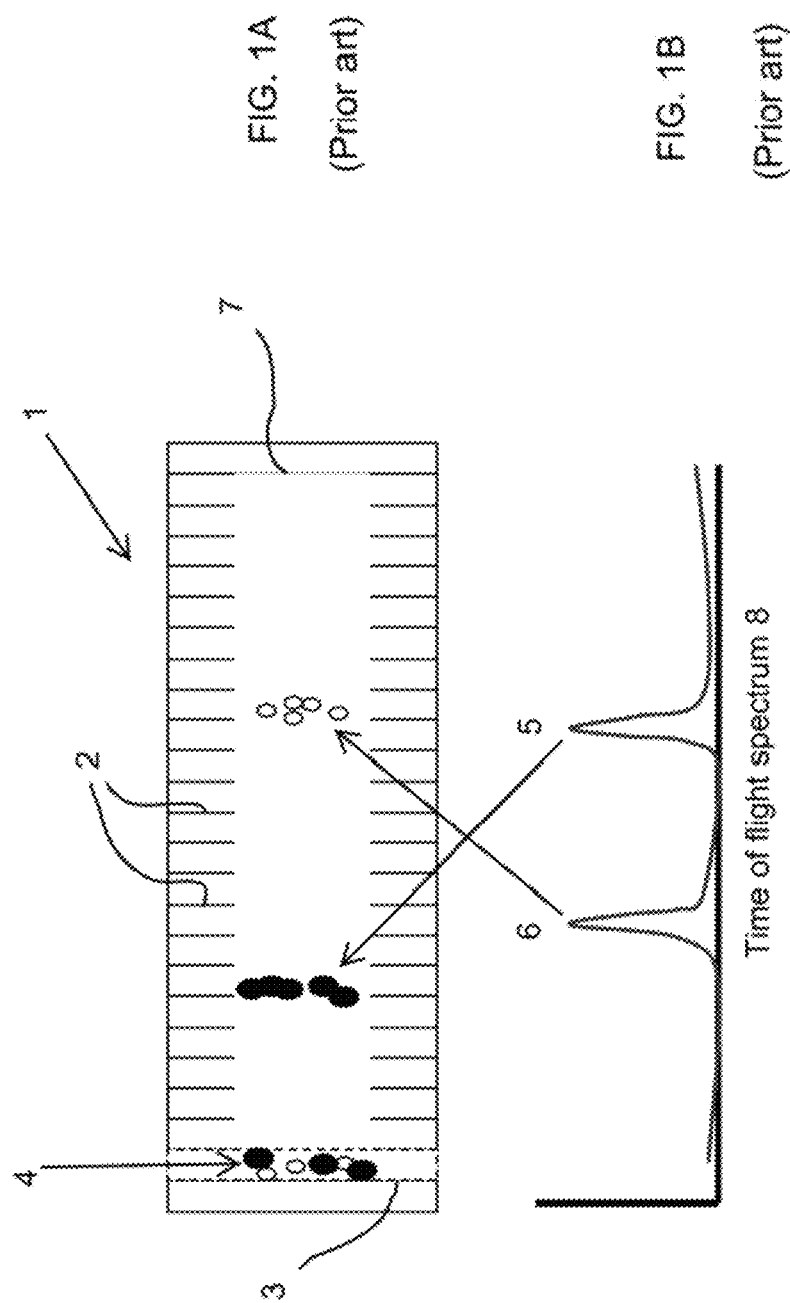

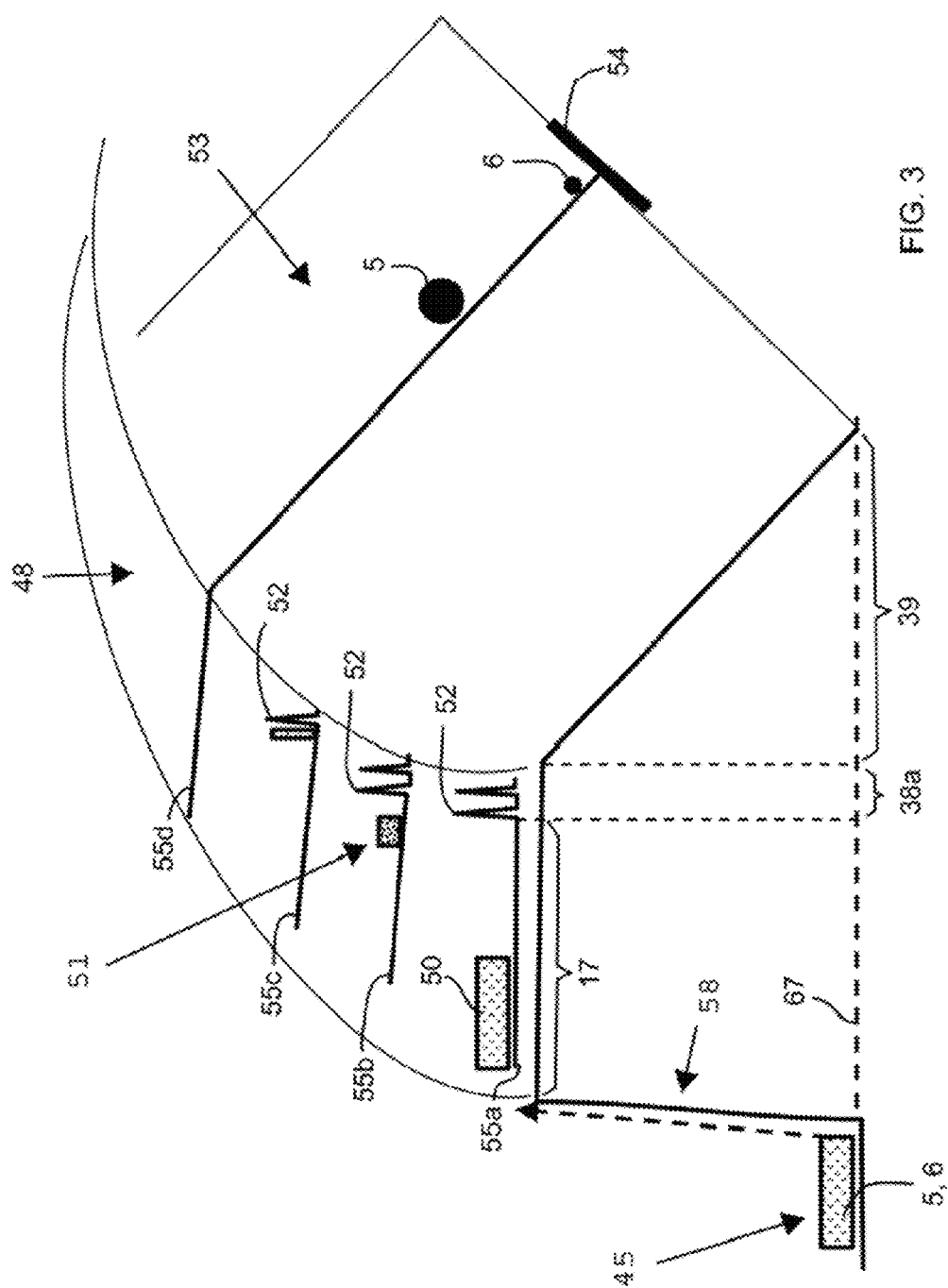

| electrode | voltage |
|---|---|
| E1 | 0 |
| E2 | 1200 |
| E3 | 1150 |
| E4 | 1100 |
| E5 | 1050 |
| E6 | 1000 |
| E7 | 950 |
| E8 | 900 |
| E9 | 850 |
| E10 | 800 |
| E11 | 757 |
| E12 | 700 |
| E13 | 650 |
| E14 | 700 |
| E15 | 550 |
| E16 | 500 |
| E17 | 450 |
| E18 | 400 |
| E19 | 350 |
| E20 | 300 |
| E21 | 250 |
| E22 | 200 |
| E23 | 150 |
| E24 | 100 |
| E25 | 50 |
| E26 | na |
| E27 | 2200 |
| E28 | 1200 |

FIG. 17A

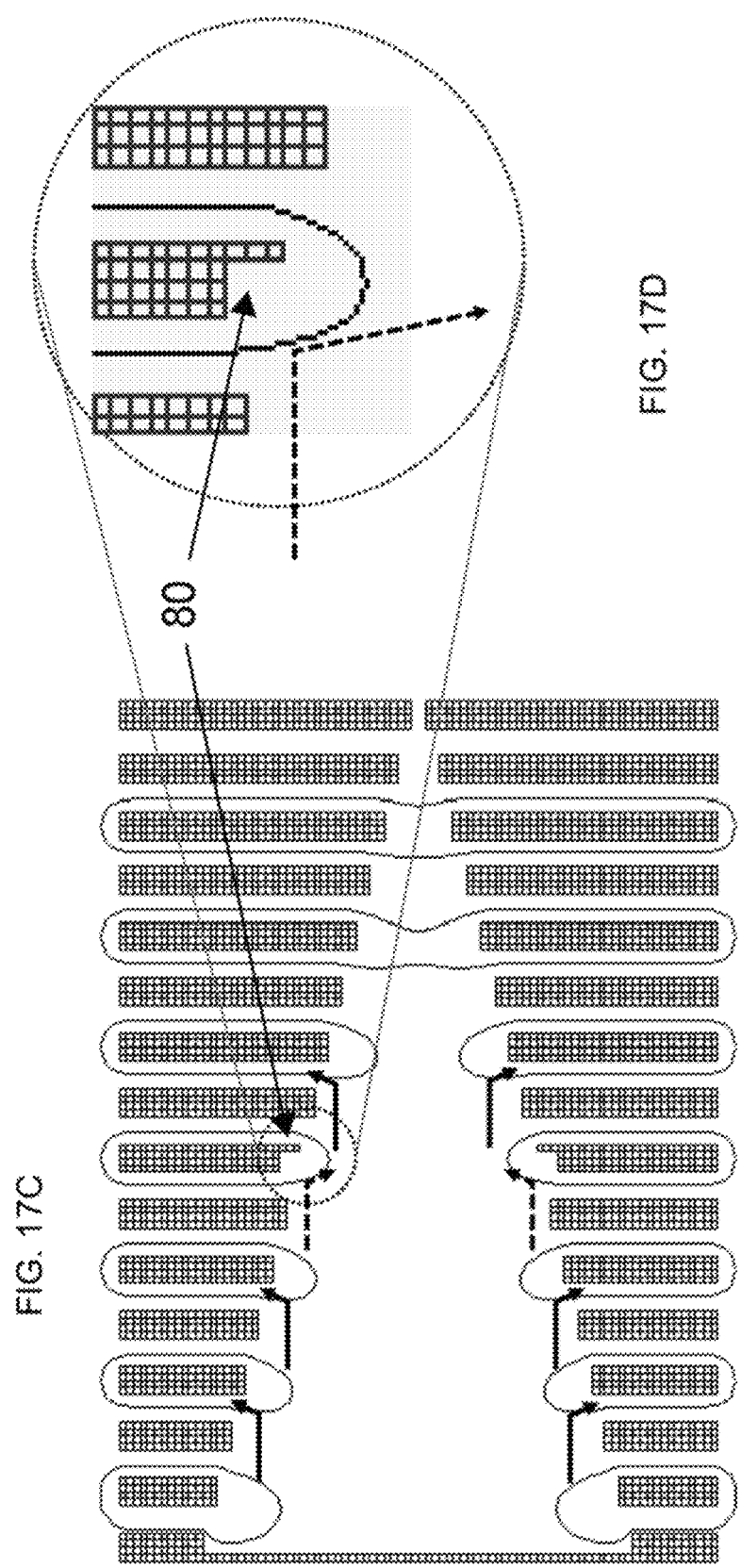

| Pres (torr) | 0.76 |
|---|---|
| Gas velx | 0 |
| Total DC gradient | 5 |
| Frequency, Hz | $5 \times 10^5$ |
| Pulse amplitude | 100 |
| Ions (Da), 10 ea | $1 \times 10^4, 1 \times 10^5, 1 \times 10^6$ |
| Simulation time | 100 ms |
| Simion Tqual | 0, grouped |

FIG. 22B

| Pres (torr) | 0.38 |
|---|---|
| Gas velx | 0 |
| Total DC gradient | 5 |
| Frequency, Hz | $5 \times 10^5$ |
| Pulse amplitude | 250 |
| Ions (Da), 10 ea | $1 \times 10^4$, $1 \times 10^5$, $1 \times 10^6$ |
| Simulation time | 100 ms |
| Simion Tqual | 0, grouped |

FIG. 23B

| Pres (torr) | 0.38 |
|---|---|
| Gas velx | 0 |
| Total DC gradient | 2 |
| Frequency, Hz | $5 \times 10^3$ |
| Pulse amplitude | 300 |
| Ions (Da), 10 ea | $1 \times 10^4, 1 \times 10^5, 1 \times 10^6$ |
| Simulation time | 100 ms |
| Simion Tqual | 0, grouped |

FIG. 24B

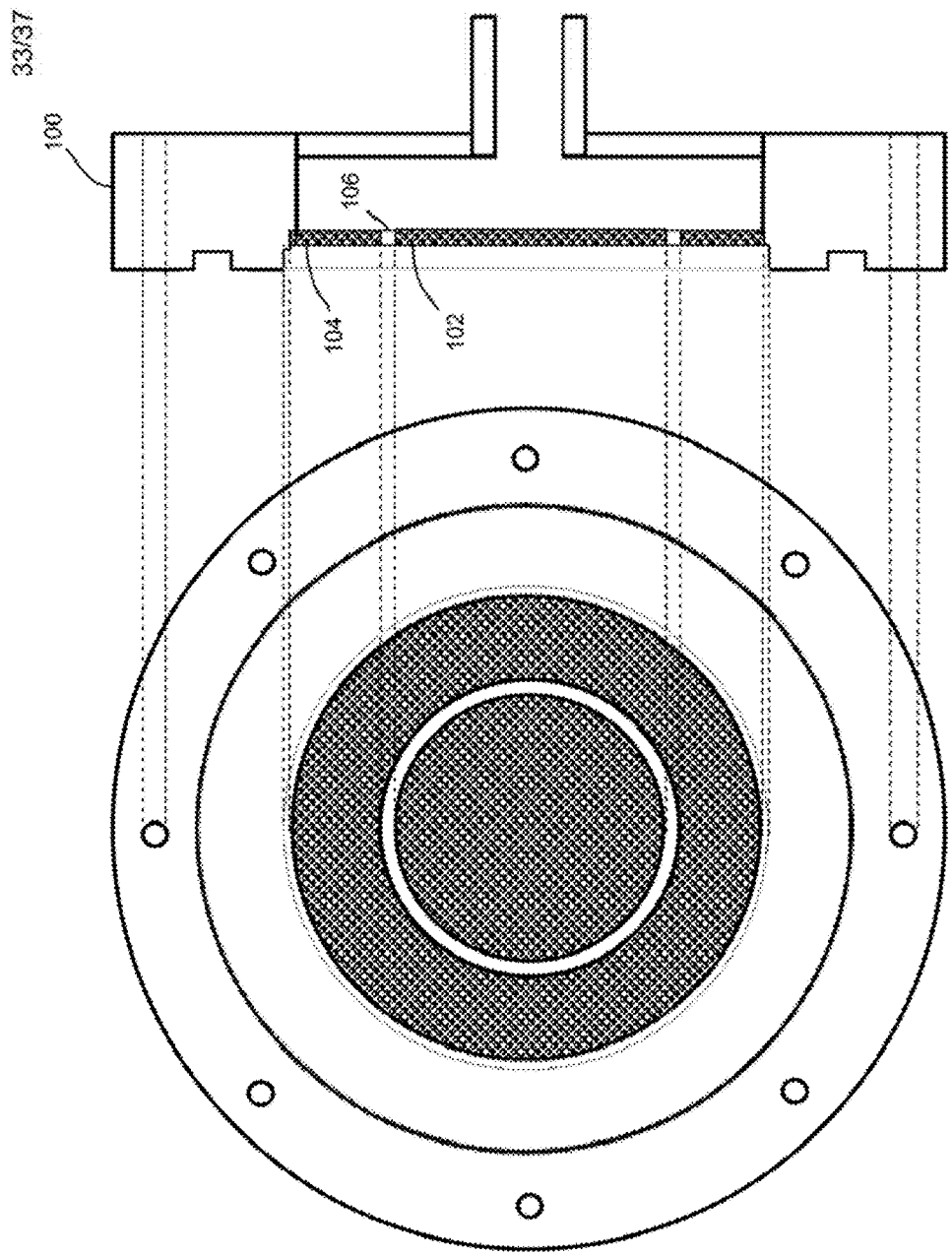

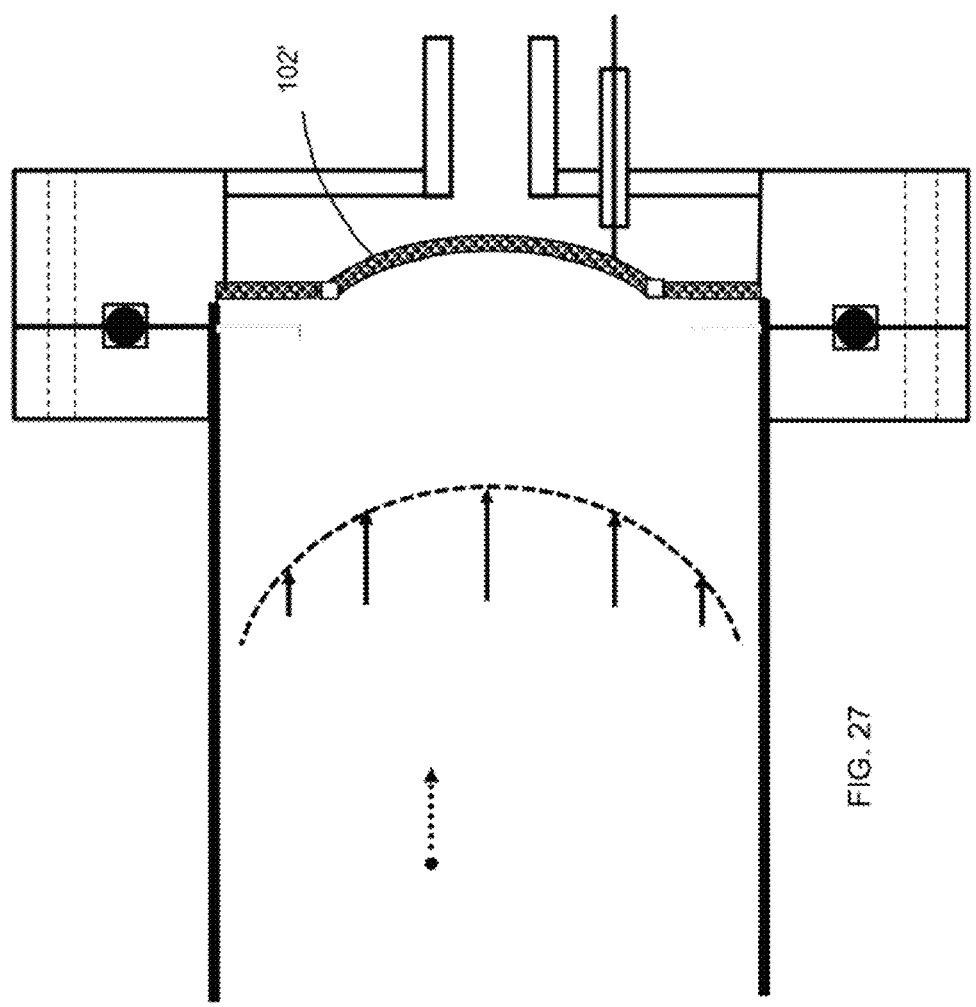

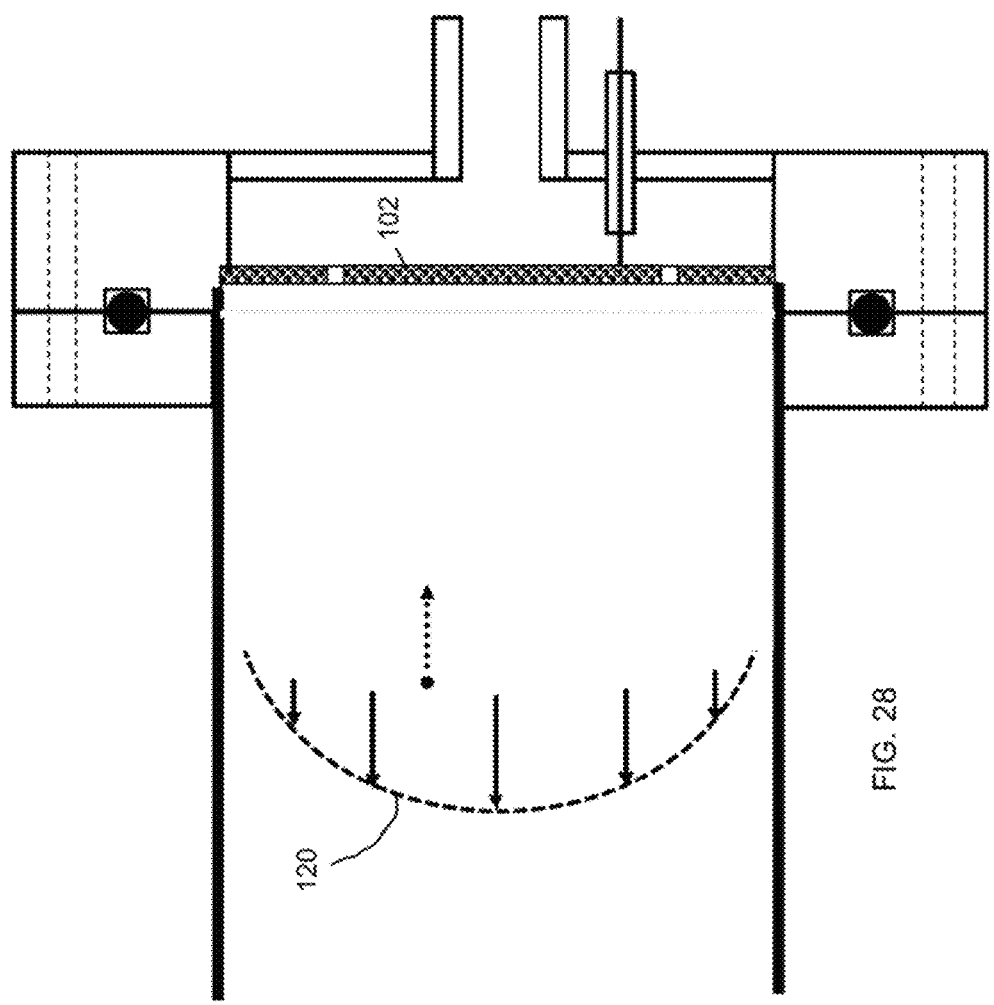

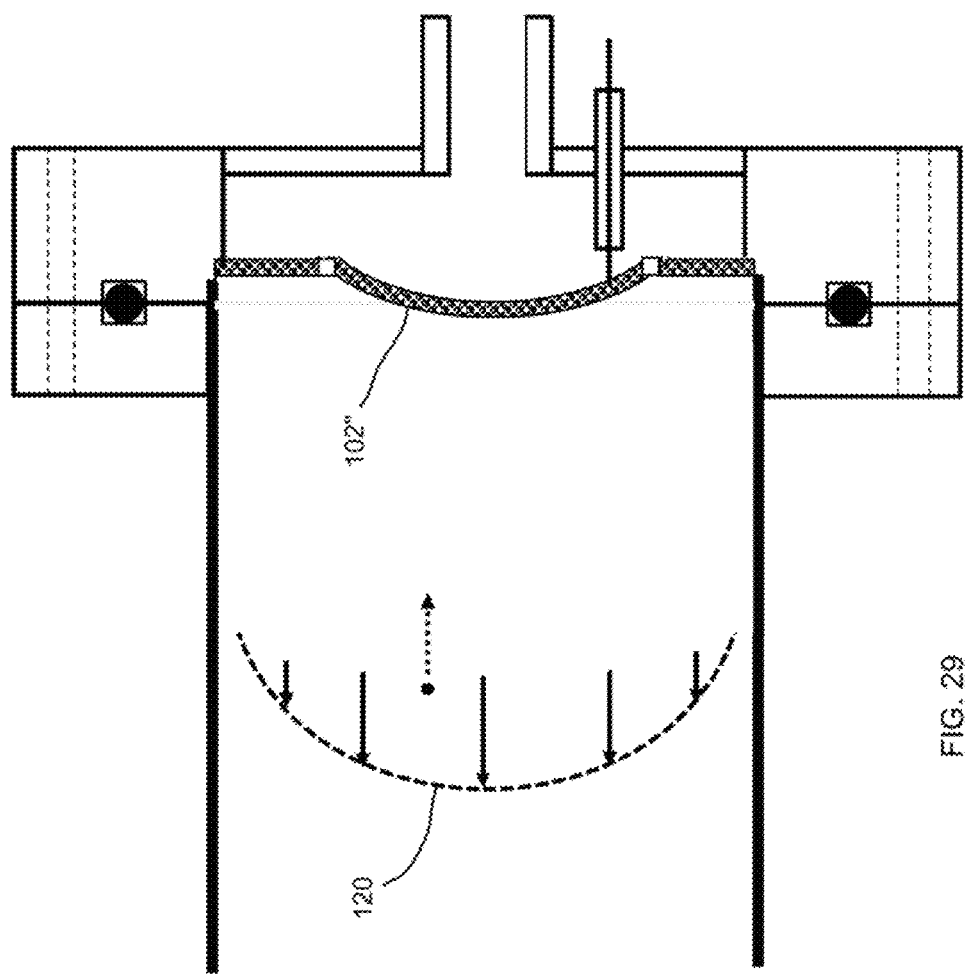

INSTRUMENTS FOR MEASURING ION SIZE DISTRIBUTION AND CONCENTRATION

CROSS-REFERENCE TO RELATED APPLICATIONS

This application claims the benefit of U.S. Provisional Patent Application No. 62/002,128 titled "Instruments for Measuring Ion Size Distribution and Concentration," filed May 22, 2014, incorporated herein by reference.

BACKGROUND OF THE INVENTION

Field of the Invention

Embodiments of the subject matter disclosed herein relate generally to apparatuses, methods and systems for measurement of ion arrival time distribution and more particularly, to devices, processes, mechanisms and techniques for measuring size distribution and/or concentration of biological materials, such as protein molecules and includes other non-biological particles such as nanoparticles.

Description of Related Art

The ability to measure and to quantify the type, behavior, and/or characteristics of biomolecular ions (e.g., measurement of individual size and local number and/or mass concentrations) is of utmost importance in a large number of applications of interest, including, for example basic biological research, medical diagnostics, drug discovery, assessment of quality of biological substances and DNA sequencing. More specifically, in the medical diagnostics area, for example, there are many reasons to measure protein sizes and concentrations, including the ability to identify a genetic disease based on the variation of size and concentration of hemoglobin.

A variety of measurement techniques have been used to characterize biomolecular substances (e.g., DNA, RNA, and proteins, including their fragments). Gel electrophoresis, high pressure liquid chromatography, dynamic light scattering, capillary electrophoresis, mass spectrometry and ion mobility spectrometry are a some of the more important techniques. Gel electrophoresis is used in clinical chemistry to separate proteins by charge and or size and in biochemistry and molecular biology to separate a mixed population of DNA and RNA fragments by length, to estimate the size of DNA and RNA fragments, or to separate proteins by charge. Nucleic acid molecules are separated by applying an electric field to move the negatively charged molecules through a gel matrix. Shorter molecules move faster and migrate farther than longer ones because shorter molecules migrate more easily through the pores of the gel. Gel electrophoresis can also be used for separation of nanoparticles. Those of ordinary skill will however recognize that gel electrophoresis is a technique that requires a substantial amount of time for completion of any given measurement. Additionally, the position of a band in a gel electrophoresis lane needs to be compared to size standards, typically molecules of known molecular weight, in order to estimate the molecular weight of the material in the band. The need to calibrate gel lanes adds to the effort involved and makes the method a relative measurement technique.

Modern chromatography instruments capably separate many types of complicated mixtures. By means of judicious choice of chromatography column packing material, many different types of biological molecules can be separated from each other so that lipids, proteins, peptides, hormones can be studied. Mass spectrometry provides a measure of an ion's mass. These instruments, while crucial to biological research, are expensive.

Differential electrical mobility analyzers may be used to determine the size distribution of biomolecular ions smaller than 100 nm. In this method, a cloud of charged aerosol particles is drawn between two electrodes, such as the annular space between two concentric cylinders. Voltage applied to the cylinders deflects particles of a predictable size into a particle detector. By scanning the voltage applied to the cylinders, the size distribution of the particles is obtained. U.S. Pat. No. 6,230,572 discloses an example of such an apparatus.

Another conventional device used to make measurements of ions is a drift tube 1, which is illustrated in FIG. 1A. In operation, voltage is applied to each of the ring-shaped electrodes 2 in such a way that the resulting electrical field inside the drift tube is constant along the longitudinal axis of the tube. A pulsed ion gate 3 is placed at the entrance to the drift tube and provides a way to introduce a pulse of ions 4 from an ion source, external to the drift tube, into the electric field generated inside the drift tube. In the example illustrated in FIG. 1A, the ion population is bimodal, i.e., it comprises a group of heavy ions 5 and another of light ions 6. An ion detector 7 is located at the opposite end of the drift tube and responds to ions when they strike the detector. In the exemplary illustration of FIG. 1A, the detector is a flat metal plate to which a current amplifier is connected and when a pulse of ions hits the detector, a momentary rise in detector current is observed, as illustrated in the Time-of-Flight (or TOF) spectrum 8 as shown in FIG. 1B for the bimodal ion group considered for this example. Ion drift tubes are commonly purged with a flow of background gas to minimize the influence of solvent vapor on drift time. Ion velocities resulting from the electrical field inside the drift tube are substantially higher than background gas velocities in the purge gas and, as a consequence, gas velocity has minimal influence on ion trajectories and does not significantly alter ion arrival time distributions. However, the performance of conventional drift tubes for massive ions having drift velocities close to the velocity of the purge gas is substantially degraded, as understood by those of ordinary skill in the applicable arts. Those skilled in the art will also appreciate the use of gas flowing countercurrent to the ions, which needs to be overcome by the ions.

Therefore, based at least on the above-noted challenges with conventional devices to measure the concentration and size of ions, it would be advantageous to have improved devices to accomplish the summarized tasks, among others, with increased measurement accuracy (particularly in embodiments operating on first principles without the need for calibration), lower cost of manufacturing and operation, reduction on the time required for measurements, and minimization or elimination of the effect of purge gas velocity on the velocity of the ions being measured, while, in some embodiments of the subject matter disclosed herein, increasing the resolution of such measurements by mathematically deconvolving from the measurements the effect of a spread in arrival times due to diffusion and non-ideal background flow velocity variations.

SUMMARY OF THE INVENTION

One or more of the above-summarized needs or others known in the art are addressed by instruments for measuring ion size distributions and concentration of ions as disclosed herein. These instruments include a body defining a flow chamber, a body defining an ion accumulation region, an exhaust port or ports, an ion detector, focusing and steering electrodes disposed inside of the chambers, an electronic gate disposed between the ion source and the flow chamber, a plurality of electrodes disposed on the body in the ion accumulation region up stream of the ion gate, a plurality of electrodes disposed on the body in the drift region downstream of the electronic gate, and a timing device configured to measure a time taken by the ions to travel from the electronic gate to the detector, from which a measurement of the size and concentration of the ions is based on an output signal from the detector and the time measured by the timing device.

The subject matter disclosed herein also includes methods and processes to measure size and concentration of ions. These methods and processes include generating ions with an ion source; introducing these ions into a chamber having reduced pressure, reducing the velocity of the ions in the resulting jet of gas by means of a jet relaxation zone or a combination of a jet relaxation zone and secondary nozzle, an ion turning device for steering ions out of the reduced velocity jet and into an ion accumulation chamber, controlling the rate and duration of ion accumulation in an ion trap, controlling the flow of the ions with an electronic gate, controlling the drift velocity of the ions as they travel through the flow chamber, measuring the time taken by the ions to travel from the exit of the electronic gate to a particle detector disposed at an end portion of the flow chamber, and measuring a current generated by the charged particles impacting the particle detector, where a measurement of size and concentration of the ions is based on the current generated by the charged particles and the time taken by the ions to travel from the electronic gate to the detector.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1A illustrates a simplified diagram of a conventional ion drift tube.

FIG. 1B illustrates a typical ion arrival time distribution.

FIG. 3 illustrates the influence of potential energy on ion motion in an exemplary embodiment of the subject matter disclosed.

FIG. 17A is a table of values for voltage applied to the electrodes in the disclosed matter. Numbers preceded by a colon enumerate an electrode's assigned number. Numbers following a colon are voltage values. In the lower panel in FIG. 17, a rectangular outline represents a simplified instrument of one embodiment of the subject matter disclosed herein. The numbers in this figure show the assignment of numbers to the electrodes.

FIG. 17C shows an embodiment of the ion accumulation region of FIG. 17B. In this embodiment, the edge 80 of the inner opening of the ring electrodes is fabricated with a step detail as illustrated in the enlarged drawing of FIG. 17D.

FIG. 17D shows an enlarged view of the step configuration of a ring electrode of FIG. 17C.

FIG. 22B is a table showing a summary of conditions that were used to generate the simulated trajectory.

FIG. 23B is a table showing a summary of conditions that were used to generate the simulated trajectory.

FIG. 24B is a table showing a summary of conditions that were used to generate the simulated trapped ion locations.

FIG. 25 shows an embodiment of detector having an assembly of porous metal components and further shown an insulating fixture (flange) serving as an end cap on a cylindrical tube that surrounds the drift region.

FIG. 27 shows the system of FIG. 26 except that the detector has a center portion that is curved to more nearly match the parabolic velocity profile.

FIG. 28 shows the system of FIG. 26 in which gas is directed away from detector and has a parabolic velocity profile.

FIG. 29 shows the system of FIG. 28 except that detector has a center portion that is curved to more nearly match the parabolic velocity profile.

DETAILED DESCRIPTION OF THE INVENTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of apparatuses, systems, or methods for measuring size and concentration of charged particles. However, the embodiments to be discussed next are not limited to these sets, but may be applied to other apparatuses, systems, or methods, including, but not limited to, the measurement of ion size, the measurement of the cross-sectional area of an ion, the measurement of the size distribution of ion clouds, the determination of the concentration of ions suspended in a gas, the determination of size and concentration of molecules in a liquid by transferring them out of the liquid and into a gas and then analyzing them, and the determination of additional properties of the particles by first separating particles according to their size before they are presented to ancillary analytical methods (e.g., laser induced fluorescence spectrometry). In other embodiments the subject matter disclosed extends ion mobility spectrometry and ion drift tubes to the analysis of charged particles, which cannot be accomplished with current ion mobility spectrometers or ion drift tubes.

For convenience, as used herein throughout, the term "ion" includes all forms of minute quantities of materials smaller than one hundred nanometers in diameter and suspended in a gas or liquid. The materials may include pure substances, such as any molecule or clusters of identical molecules characterized with a molecular weight. The materials may also include mixtures of materials, such as aggregated molecules having different molecular weights. The term charged-particle refers to any minute form of material that carries an electric charge, examples of which include, but are not limited to, particles isolated from a human or an animal serum, such as lipoproteins or exosomes, particles released from a combustion process, smoke particles, dust particles, nanoparticles, assemblies of molecules, clusters of protein and/or lipid molecules, atmospheric aerosols, nanolipid particles, nanolipid disks, and clumps of such particles.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures, or characteristics may be combined in any suitable manner in one or more embodiments.

Figure 2A:
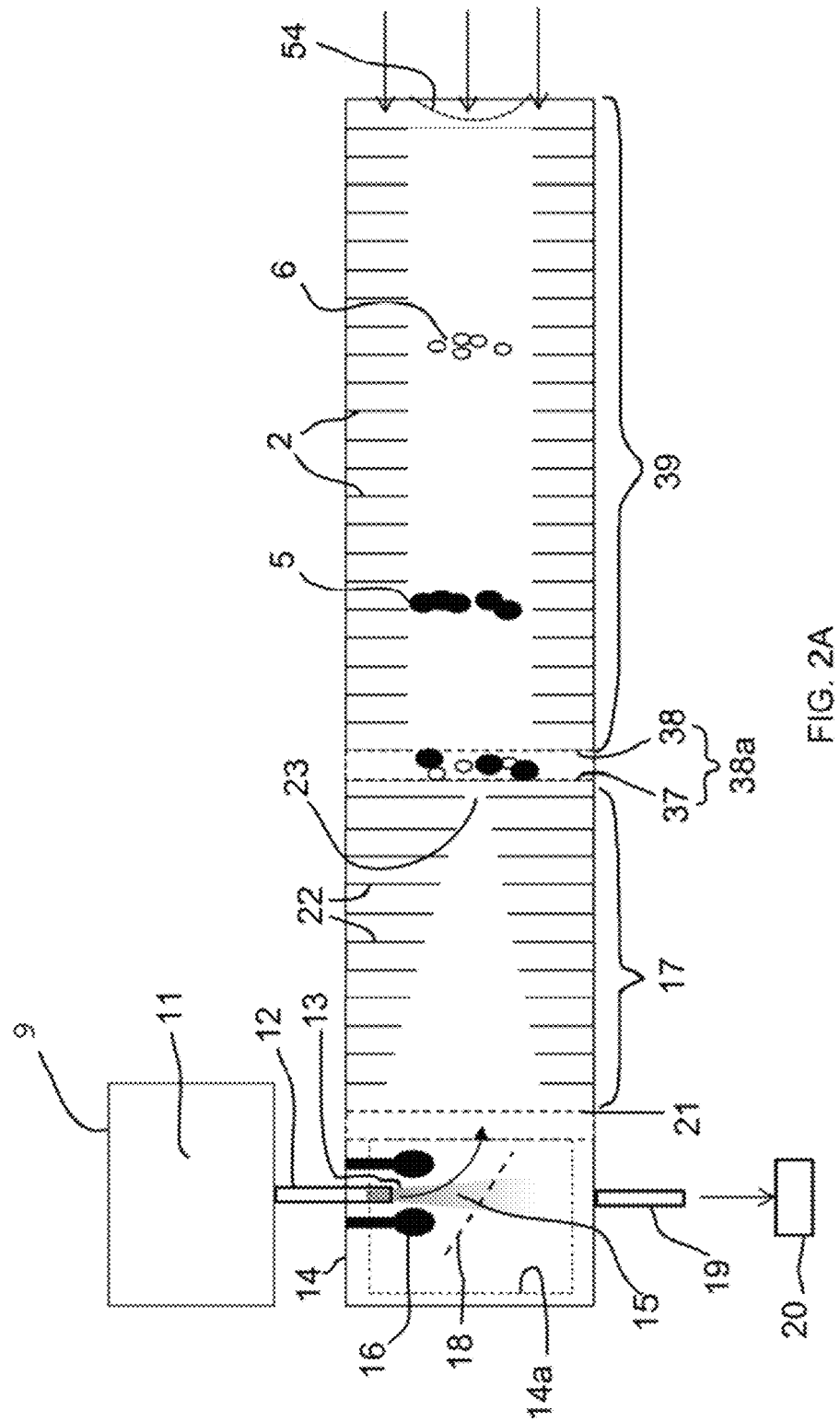
FIG. 2A illustrates an ion mobility spectrometer according to one exemplary embodiment of the subject matter disclosed.

An exemplary embodiment of an ion mobility spectrometer according to the subject matter disclosed is illustrated in cross-section in FIG. 2A. As shown, an ion source 9 (as, for example, an electrospray source, a nebulizer, a flame, a combustion engine, or a gas-phase chemical reactor) generates gas-borne ions disposed in a region of atmospheric pressure 11 that are introduced through a nozzle 12 to form an ion-laden jet of gas 13 moving at high velocity into the body of a first chamber, called a jet relaxation chamber 14, this body defining a chamber is pumped by a vacuum pump 20 to introduce the ions to reduced pressure. Ions flow through the nozzle 12 (which, in one embodiment, comprises a small orifice having a diameter in the range of about 10 to about 1000 microns or preferably from about 200 to about 600 microns) at sonic velocity, where the downstream pressure in the jet relaxation chamber 14 is any value less than 0.5 bar so as to assure choked flow conditions at the nozzle 12, i.e., the gas jet and particles have sonic velocities at the point of minimum area of the nozzle 12. As illustrated, in the jet relaxation chamber, a jet relaxation region 15 is formed by means of a cylindrical restriction 16 which is configured to reduce the velocity of the jet of gas-borne ions by de-accelerating the jet without blocking the jet. In some embodiments the cylindrical restriction nozzle 16 is adjustable with respect to nozzle diameter and position within the jet relaxation region 15 so as to allow better control of the gas velocity in the jet relaxation chamber 14. As the ion-laden jet 13 flows into the jet relaxation region 15, conditions are established that help to introduce ions into the ion accumulation region 17 by substantially reducing the influence of gas velocity on the dynamic behavior of the ions to be measured. Conditions of low gas velocity and pressure are desirable so that gas velocity does not impede substantially the steering of ions into the ion accumulation region.

Figure 2B:
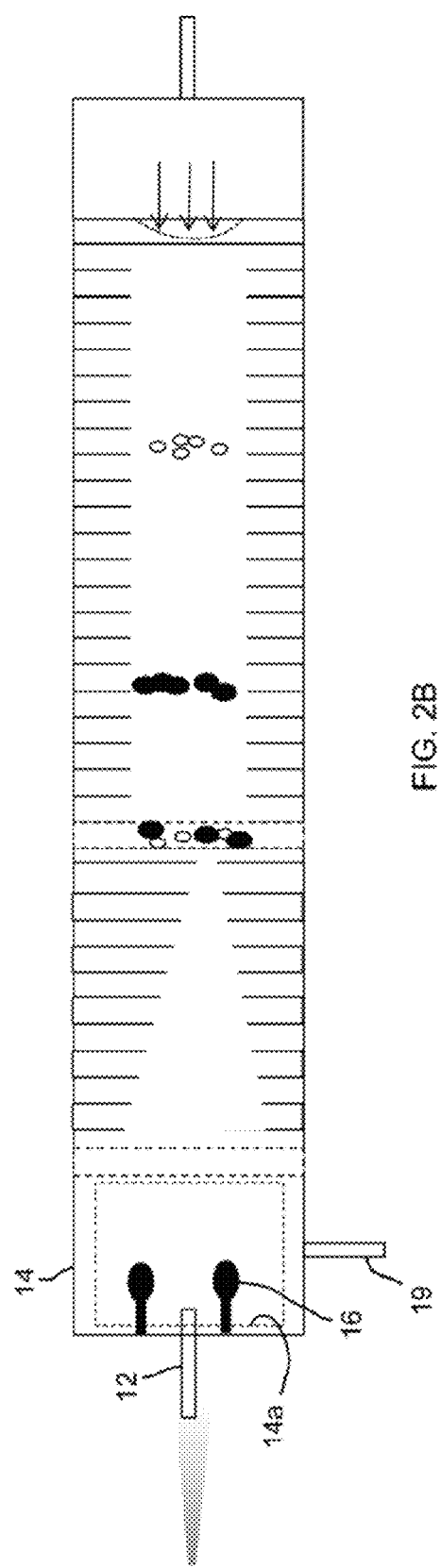
FIG. 2B illustrates an ion mobility spectrometer according to one exemplary embodiment of the subject matter disclosed.

The nozzle 12 is maintained at ground potential while the surrounding metal wall of the jet relaxation chamber 14a, is maintained at a high potential on the order of 10 kV. The use of a nozzle that protrudes into a region surrounded by a wall maintained at a higher potential provides an economical means to inject ions that were generated at ground potential onto a high potential surface, described below. The jet of gas carries positively and negatively charged ions up and through a positive polarity potential valley. Without the influence of the gas, only negative ions could travel unimpeded up a positive potential valley and positive ions would be repelled in the opposite direction. Based on potential energy consideration, it was chosen to operate with positively-charged ions and an instrument was designed that first lifts positively-charged ions via the gas jet to an elevated positive potential surface from which they eventually roll down and through the remaining portions of the apparatus, ultimately to ground potential where they are detected electrically. Positively charged ions are subjected to a repulsive force created by the positive potential applied to the wall 14a of the jet relaxation chamber 14. The repulsive force acts more strongly on small ions and prevents them from travelling up the potential hill. Large ions suffer more collisions with background gas molecules which ameliorate the repulsive force. This design feature excludes small positive particles from entering the jet relaxation chamber and minimizes signals from solvent ions. Small and large negatively charged particles will travel up the potential hill. As described in more detail below, FIG. 2A further shows a second nozzle 16, a screen 18, a port 19 from jet relaxation chamber 14 to vacuum pump 20. Additionally, the figure shows an ion accumulation region 17 having ring electrodes 22 and a narrow exit 23. Following the narrow exit 23 is a grid 37 and a grid 38 which together form an electric gate 38a. Following the ion accumulation region 17 is a drift region 39 also including a set of ring electrodes 2. A detector 54 is located at the end of the drift region. FIG. 2B shows an embodiment having identical elements as FIG. 2A, except that the first nozzle provides ions coaxially with the system and therefore the system does not require a screen 18.

Figure 2C:
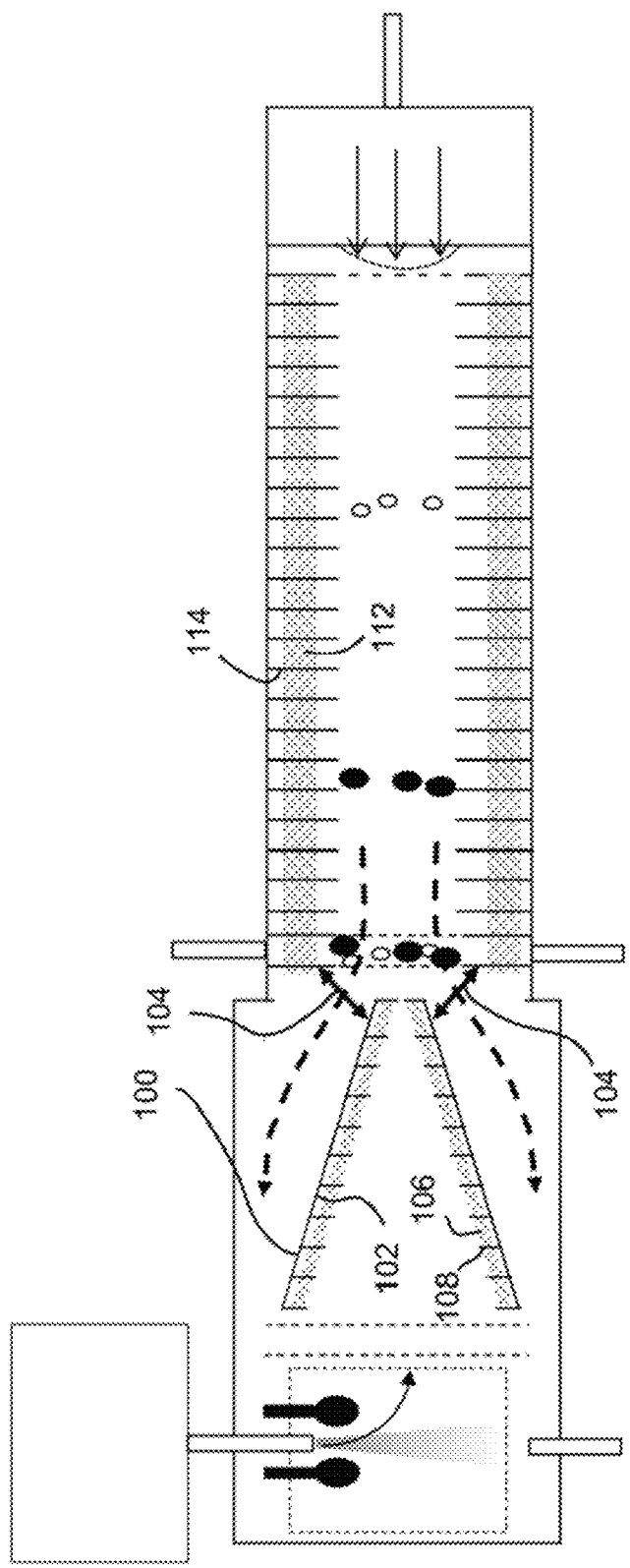
FIG. 2C illustrates an ion mobility spectrometer according to one exemplary embodiment of the subject matter disclosed.

An alternative configuration for the ion accumulation region is shown in FIG. 2C wherein the outer surface 100 of a cone shaped in a manner such that the internal angle of the cone and the angle describing the outer surface are equal. In cross sectional view, as shown, the inner surface 102 and the outer surface 100 are parallel surfaces. The inner and outer surfaces don't necessarily have to be parallel. The main idea is that there is room on the outside of the cone electrode configuration for gas to flow between the cone electrode configuration and the enclosure, yet remain within the enclosure of the accumulation region. An embodiment of this alternative design maintains the opening illustrated by the double pointing arrows 104 to be equal or greater in area (the area of a frustrum of a cone) to the area of the detector. This embodiment provides a minimal restriction to gas flowing from the entrance of the drift tube towards the ion accumulation region. The minimal restriction to gas flow minimizes compressibility of the flowing gas and provides a flow pattern that minimizes swirling or turbulence at the entrance to the drift tube. The dashed arrows illustrate streamlines of gas flowing smoothly from the entrance to the drift tube, towards the exit of the ion accumulation region, then passing along the outer wall of the ion accumulation region as resulting from this alternative embodiment. The figure also shows dielectric material 106 located between the ring electrodes 108 of the accumulation region and further shows dielectric material 112 located between the ring electrodes 114 of the drift region.

The process of lifting ions from ground potential to a higher potential plateau 48 is illustrated in FIG. 3 where a 3-D potential energy surface is used to describe the influence of potential on the motion of an ion according to the present invention. Utilizing, e.g., the embodiment of FIG. 2A, a cloud of ions 45 is released from the nozzle 12 and carried into the first chamber 14 that is surrounded by a wall 14a maintained at HV. The force of the jet of gas pushes the ions up through a potential barrier 58 (consistent with FIG. 10), which is produced by the electrified wall of the jet relaxation chamber 14a, where they rise to potential plateau 48 and enter the ion accumulation region 17. The illustration in FIG. 3 provides one way to visualize an ion's temporal history as it travels through the instrument disclosed herein. A time sequence with time slices, 55a, 55b, 55c, 55d show a cloud of ions at different time periods. Period 55a precedes period 55b, etc. Ions thrust upon a high potential plateau 48 experience a pulsed high voltage applied to the ring electrodes in the ion accumulation region and oscillate up and down while at the same time they are guided by a DC potential towards the exit 23 to the ion accumulation region. Beginning with time sequence 55a, ions 50 enter the ion accumulation region 17, where local electric forces applied during time period 55b compresses the ions 50 into a narrow bunch 51. At a later time period 55c, a potential 52 applied to the first grid 37 is lowered and the ions stack up against a potential barrier created by a potential 52 applied to a second grid 38. At a later time period 55d, a potential applied to a second electrode 38 is reduced, allowing the ions to escape from the blocking barrier and slide down the potential hill 53 towards the detector 54. The ions experience a resistance caused by collisions with the background gas as they slide down the hill. Large ions experience a larger resistance and slide more slowly than smaller ions. The smallest ions 6 strike the detector 54 before the larger ones 5 strike the detector.

In operation, gas, along with a small number of neutral particles, and an appropriate number of charged particles are drawn through jet relaxation chamber 14, ion accumulation region 17 and drift region 39 by virtue of the reduced pressure inside of the instrument along with electrostatic forces. The in-flowing ion-laden gas results in the formation of an expanding jet. Gas conditions in the jet, i.e., gas velocity and pressure, are such as to carry the particle-laden gas towards the screen 18. Initially, the ion-laden gas jet is confined closely to the centerline of the nozzle 12. After the gas travels a certain distance (e.g., about 3-5 cm for some embodiments), the jet relaxes due to the presence of a second nozzle 16 in some embodiments. The second nozzle 16 acts as a pumping restriction and prevents the jet of gas to form a fully developed 15 deg half-angle expanding cone. Those experienced in fluid dynamics will understand the consequences of a fully formed jet and recognize that in a reduced pressure chamber, i.e., a chamber having less than 0.5 atm pressure, an expanding jet will extend many cm into the chamber before it collapses. Here, the second nozzle 16 disrupts the jet. The second nozzle 16 generates a modified jet of gas with much lower gas velocity compared to the initial jet, which in turn, produces a flow of ions having a velocity suitable for interacting with the screen 18 in a manner that turns the ions away from the centerline of the jet and into the ion accumulation region when a potential is applied to the screen 18.

Referring again to FIG. 2A and the jet relaxation chamber 14, the ion-laden jet of gas 13 approaches fine mesh screen 18 at approximately 45 degrees. The screen 18 is connected to an appropriate voltage source having a voltage which electrostatically repels ions opposite in polarity to the polarity of the applied voltage orthogonally towards the entrance to the ion accumulation region 17. Gas emanating from the jet relaxation region 14 flows unimpeded through the screen and escapes from the jet relaxation chamber by means of port 19 connected to vacuum pump 20. In one embodiment, the screen (steering electrode) 18 is a flat fine-mesh screen of the type manufactured by Precision Eforming, LLC, such as an 85% transmission electroformed Ni mesh that has 100 lines/in, each 0.00078 inches thick. The meshes should be as transparent as possible. Currently, 75-90% transmission meshes are available. In another embodiment the screen 18 may be parabolically, hyperbolically or spherically shaped for the purpose of steering ions more effectively into the ion accumulation region. Although the embodiment illustrated in FIG. 2A includes only one steering electrode, it should be understood that the scope of the subject matter disclosed herein includes embodiments that may use a multiplicity of steering and focusing electrodes. Positively and negatively charged particles that reach the deflection grid 18 will become separated from each other by the voltage applied to the screen.

In one embodiment, positive voltage is applied to the steering electrode 18 which deflects positive ions into the accumulation region while attracting the negative ones. The magnitude of the voltage applied to the screen diverts ions according to the velocity of the ions in the gas jet, the magnitude of charge on the ions and the mass of the ions. Appropriate choice of screen voltage, along with voltage applied to grids 21 provides a means to optimize the transfer of ions away from the jet and into the ion accumulation region. The voltage applied to the screen 18 can be a DC voltage or a pulsed voltage. A DC voltage will steer ions continuously into the ion accumulation region. A pulsed voltage will steer ions during the moment the screen is provided with a voltage pulse. A pulsed voltage provides a means to regulate the transfer of ions into the ion accumulation region. One set of exemplary voltages applied to the screen is listed in a table in FIG. 17A. These voltages can be scaled by factors between 1× and 10×.

After the steering electrode 18 deflects positive ions towards the ion accumulation region, the ions then pass through one or more fine mesh grids 21 and enter the ion accumulation region. The grids 21 provide a means to drag ions electrostatically through a reduced pressure gas by means of an electric field produced by voltage applied to the grids 21. After the particles pass through the grids 21, an electric field generated by voltages applied to electrodes in the ion accumulation region 17 begins to control ion motion in the ion accumulation region. The ion accumulation region has been termed an ion funnel. Ion funnels as understood by practitioners in the field of mass spectrometry and ion mobility spectrometry are used to capture ions that are spread over a large area, such as a 5 cm$^2$ opening, and draw them into the interior of the funnel and towards a narrow exit aperture on the funnel that typically defines the entrance to a mass spectrometer. As known in the art, an ion funnel is powered by DC and RF power sources connected to ring electrodes disposed as components in an ion funnel. DC power is used to generate an electric field that guides ions to travel through the ion funnel. RF power is provided for a means to focus ions towards the centerline of the funnel as they travel through the funnel.

Ion accumulation is the process of introducing ions into the ion accumulation region 17 at a rate that is faster than the rate ions escape from the ion accumulation region. Due to the design of the ring electrodes dispensed in the ion accumulation region, along with the voltages applied to the ring electrodes and further as a result of gas pressure in the ion accumulation region, ions are guided towards the increasingly narrow exit end 23 of the ion accumulation region. By choosing an appropriate DC voltage, the magnitude of the RF pulses, the frequency of the RF pulses, the internal diameter of the ion accumulation region, the conical shape of the ion accumulation region, and gas pressure, it is possible to control the rate at which ions escape from the exit end 23 of the ion accumulation region 17. It is further possible to prevent ions from escaping from the accumulation region, and under appropriately chosen conditions, the ion accumulation region functions as an ion trap.

An ion accumulation module provides a means to increase the signal level of an ion detector located downstream of the ion accumulation region. The signal level is increased because ion accumulation followed by a means to release simultaneously all of the trapped ions leads to a cloud of ions that carries a large number of ions, thus inducing a large current pulse when the cloud strikes the detector as compared to a cloud of ions composed of a small number of ions. A larger current pulse enables trace species to be detected. The capability to accumulate and release simultaneously the trapped ions is an important feature of the information disclosed herein.

The ion accumulation region 17 is dispensed with a plurality of ring electrodes. The center bore of the first electrode defines the opening to a funnel shaped chamber with each successive electrode having a smaller internal bore. In one embodiment, twelve ring electrodes are aligned axially and each is separated from the next electrode by identically-sized dielectric spacer rings having centered bores equal to the bore on the previous (i.e., the nearest upstream) electrode. Grids 21, along with DC voltage applied to 22 in the entrance to the ion accumulation region 17 are configured to control the velocity of the ions in the ion accumulation region causing them to travel towards the narrow exit 23 of the ion accumulation region. The ring electrodes are further described below.

A cylindrical outer chamber and a stack of ring electrodes, along with dielectric spacers disposed between the ring electrodes comprise the ion accumulation region. The inner diameter of the ring electrodes decreases along the longitudinal axis of the region. In one embodiment, the first ring in the ion accumulation region has an internal diameter of 3.2 cm. the internal diameter of subsequent ring electrodes decreases proportionally to a cone with a 15 deg half angle. In this embodiment, twenty one ring electrodes are disposed in the cylindrical chamber and the final ring electrode has an internal diameter of 0.05 cm. Dielectric spacers, such as rings fabricated with Lucite® or Teflon® or Kapton® are positioned between the ring electrodes. In one embodiment the ring electrodes are 10.0 cm outside diameter rings, 0.040 cm thick, fabricated from stainless steel. The dielectric spacers are 10.0 cm outside diameter rings, 0.50 cm thick having internal diameters equal to the internal diameter of the proceeding ring electrode. In this manner, the dielectric spacer appears hidden to ions travelling through the stack of ring electrodes. The stack of ring electrodes along with dielectric spacers inserted between the ring electrodes is known to those skilled in the art of mass spectrometry as an ion funnel. Patents, incorporated herein by reference, U.S. Pat. No. 6,583,408 B2, U.S. Pat. No. 6,107,628 A, U.S. Pat. No. 6,818,890 B1, U.S. Pat. No. 7,888,635 B2, describe exemplary prior art of the ion funnel.

In one embodiment of the ion accumulation region, the ring electrodes are fabricated from screen material rather than from sheet metal. When ring electrodes, fabricated from screen material, are disposed in the ion accumulation region, gas flowing through the ion accumulation region is no longer 'funneled' by the solid metal rings and is free to pass through the openings in the screen. This design for electrodes provides a more uniform flow of gas through the ion accumulation region. The screen material may be a fine mesh or a coarse mesh.

Figure 4:
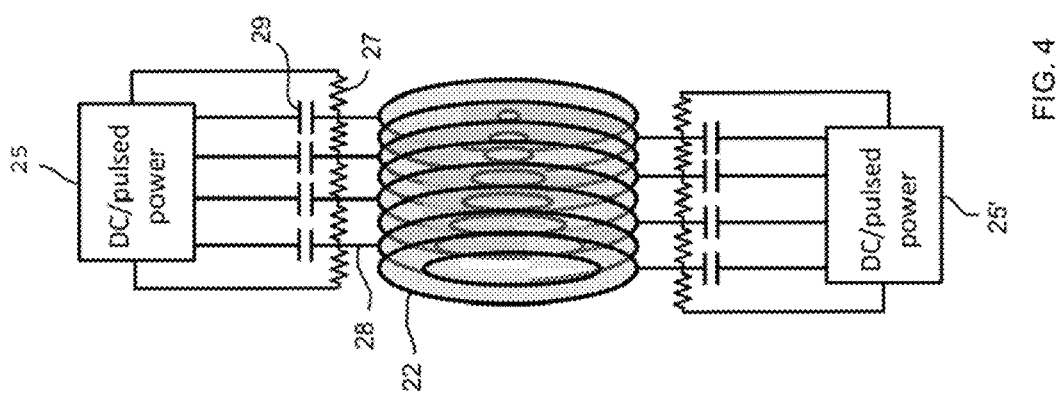
FIG. 4 illustrates the placement and alignment of ring electrodes in the ion accumulation region of yet another exemplary embodiment of the subject matter disclosed.
Figure 5:
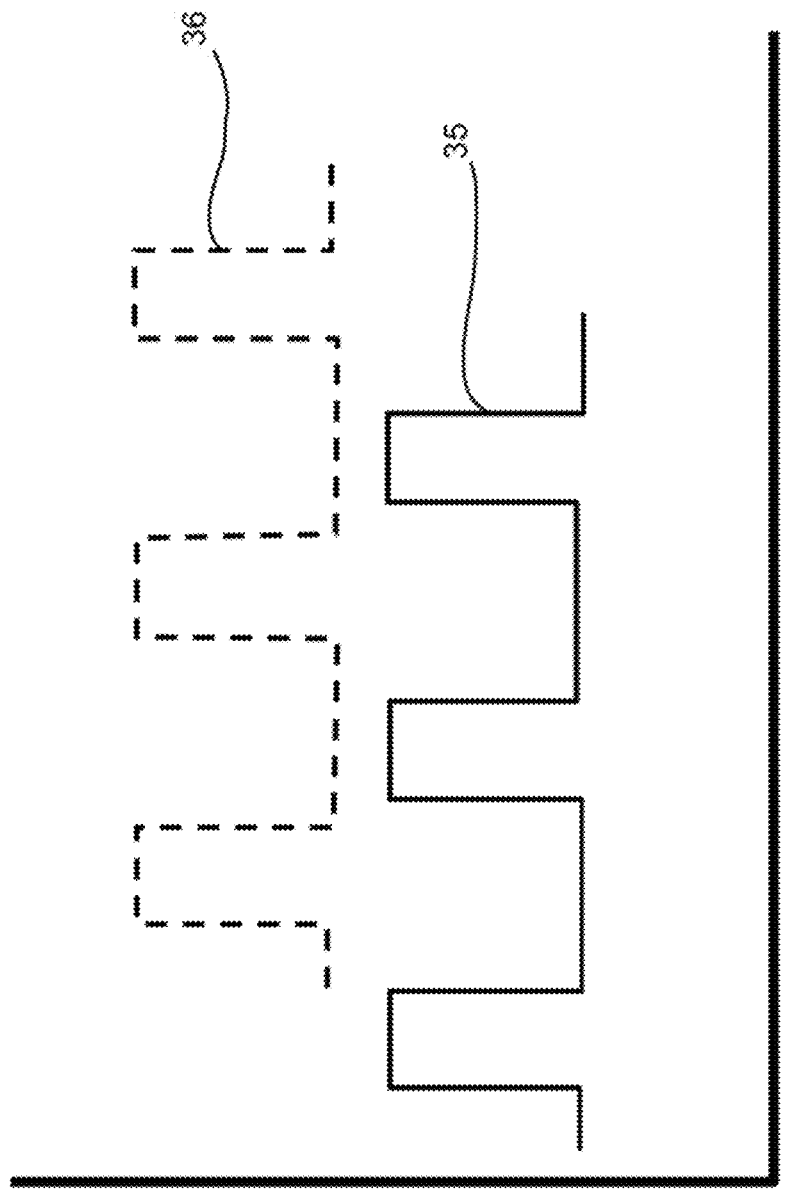
FIG. 5 illustrates a pattern of electrical pulses applied to the ring electrodes in yet another exemplary embodiment of the subject matter disclosed.

In the embodiment illustrated in FIG. 4 the ring electrodes 22, which are exemplary of electrodes in the ion accumulation region 17 shown in FIG. 2A, are connected to voltage sources 25, 25' that provide DC and high voltage pulsed power in several alternative configurations. In a first configuration, only a DC power source is connected to the electrodes in a manner in which the DC power is distributed by means of a voltage divider in which electrical attachments 28 between resistors 27 distribute divided voltage to each ring electrode. In a second embodiment the DC voltage is 0. In a third embodiment DC voltage (either 0 or non-zero voltage) and pulsed HV power are connected to the ring electrodes in a manner such that a first set of electrodes receives HV pulsed power while a second set receives no HV pulsed power. This is accomplished by rapidly turning on and off one of the HV power sources (e.g., 25) by means of a pulse generator while maintaining the second power source (e.g., 25') at 0 volts. Later, after a time period, the first HV power source is switched to 0 volts and the second HV power source is rapidly turned on and off by means of a second pulse generator. FIG. 5 is an illustration of the time varying voltage that is applied to the ring electrodes in the ion accumulation region 17. The horizontal axis in FIG. 5 represents a time period and the vertical axis represents voltage. The two plots are off-set vertically. In one embodiment, the baseline of each plot is set to 0 volts. Those skilled in the art of applying pulsed voltage to a DC circuit will appreciate the use of electrical capacitors 29 between the pulsed power sources and the rings. The solid line 35 depicts the time-varying voltage applied to capacitors connected to a first set of electrodes and the dashed line 36 depicts the time-varying voltage applied capacitors connected to a second set of electrodes. The combination of DC and HV pulsed power causes the ions in the ion accumulation region 17 to drift towards the narrow exit end 23 of the ion accumulation region. HV pulsed power illustrated in FIG. 5 has a magnitude of 200 volts, which voltage is exemplary and voltages between 0 and 1000 volts are applicable. The HV pulses have a width that is commensurate with 10 kHz to several MHz pulse rates with 500 kHz as a typical value.

Referring again to FIG. 2A, those of ordinary skill in the applicable arts will appreciate that, during the time ions accumulate in the electronic gate 38a following time sequence 55c in FIG. 3, diffusion will tend to disperse the ions, although the effect of voltage applied to the gate electrodes will help to minimize dispersion caused by diffusion. As discussed above, in one embodiment of the ion accumulation region, one or more fine mesh screens 37, 38 are disposed after the narrow final ring electrode 23. The fine-mesh screens are connected to pulsed voltage sources for the purpose of controlling the rate ions escape from the ion accumulation region. These fine mesh screens comprise an ion gate and by momentarily adjusting voltage provided to the screens, ions are blocked from escaping the ion accumulation region for a period of time called the ion accumulation time, as illustrated in time sequence 55c in FIG. 3. The blocking condition is transformed into a gating condition by altering the voltages provided to grids 37 and 38. After an ion accumulation time, voltage provided to the gate screens can be adjusted to allow ions to be guided into a third chamber called the drift region 39, as illustrated in time sequence 55c and 55d in FIG. 3. In one embodiment a first screen 37 is provided with a voltage high enough to block the ions from escaping the ion accumulation region while a second screen is also provided with a voltage high enough (55c) to block the ions from passing through the second screen 38. After an optimized brief time period, all of the ions that were accumulated in the ion accumulation region are accumulated for a second time period in a region between a grid 37 and a second grid 38. Then during the final time sequence 55d, ions are released from the region between the first and second screens by providing a lower voltage to the second grid (38). In this manner, the ions are released 52a from a second trapping situation and pass freely into the drift region 39.

Placement of the electrodes for the electronic gate 38a (or gate electrodes 37, 38) downstream of the ion accumulation region 17, as explained, allows trapped ions that are moving near the exit to the ion accumulation region to be blocked by the voltage applied to the electronic gate 38a. In some embodiments, the electronic gate 38a is held at a blocking voltage for a period of time ranging from about 0.01 to about 1 second, so that the flow of ions can be controlled at this gate position, increasing the ultimate signal levels of ions arriving at the detector 54, following their release from the region near the electronic gate 38a.

Figure 6:
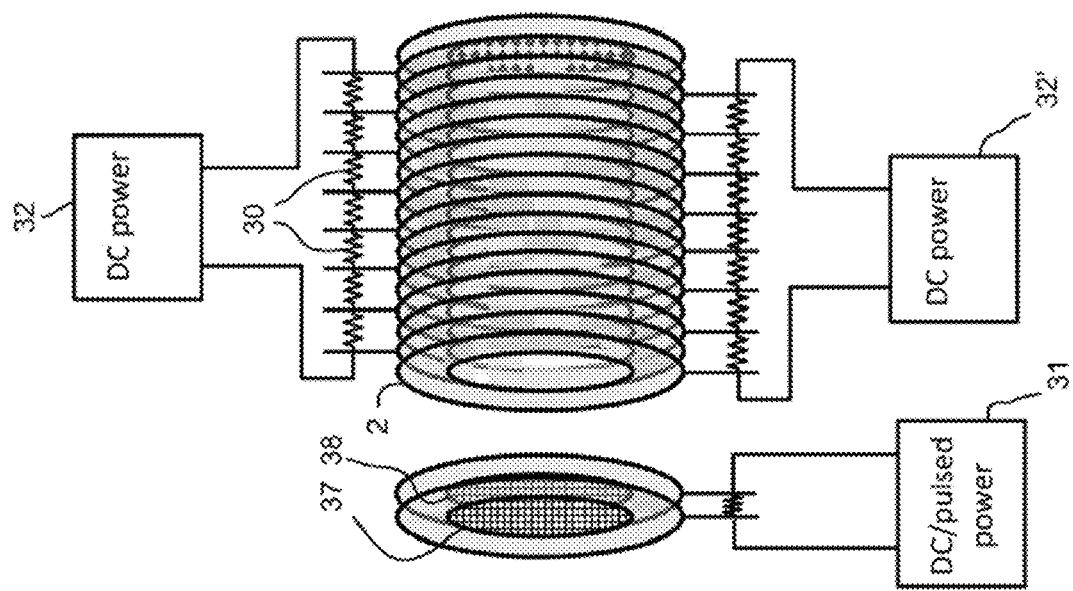
FIG. 6 illustrates the placement and alignment of ring electrodes in the drift region of yet another exemplary embodiment of the subject matter disclosed.

FIG. 6 further illustrates the electrodes of a drift region 39 according to one exemplary embodiment of the subject matter disclosed. As shown, one or more fine mesh screens 37, 38 having an open area of 85 percent are disposed upstream of the entrance to the drift region and by means of voltage provided to these screens from DC/pulsed power supply 31, a cloud of ions can be released into the drift region. In FIG. 6, the ring electrodes 2 attached to the voltage divider network, that includes resistors 30 powered by DC power supplies 32 and 32', comprise the drift region 39 of FIG. 2A The drift region 39 of the disclosed material contains a set of ring electrodes. In some embodiments, electric fields are established in the drift region by means of ring electrodes and ring electrodes equipped with a fine mesh grid. In one embodiment, the ring electrodes in the drift region are fabricated from stainless steel. The combination of a ring electrode and a fine mesh grid is a grid electrode. Practitioners in the art of fabricating mass spectrometers will appreciate the care needed to prevent electrical discharge from high voltage electrodes that are operated in a reduced pressure environment. The edges of the ring electrodes were polished to remove burrs and thus minimize the possibility of electrostatic discharge from burrs.

By substantially reducing the pressure in the drift region 39, the challenge of measuring ions having low drift velocities (for example, heavy ions or charged nanoparticles) is substantially ameliorated because aerodynamic drag is reduced, thus allowing ions to travel faster for a given electric field strength than the background gas velocity. It is known that drift velocity scales inversely with pressure, and to a first approximation, gas flow velocity in the drift region also scales inversely with pressure. One of the advantageous aspects of introducing ions orthogonally to the direction ions fly in the drift region by means of a deflection screen 18 in the jet relaxation chamber 14 is the provision of a method to transport charged particles into a uniform low velocity gas, along with acceptable drift times for the ions, on the order of 400 ms in some embodiments. Embodiments similar to the one illustrated in FIG. 2A are thus capable of transporting a gas at atmospheric pressure, along with charged and uncharged particles entrained in the gas, through an orifice, after which passage ions of a selected polarity are released into a flow of background gas in a drift region.

Figure 7:
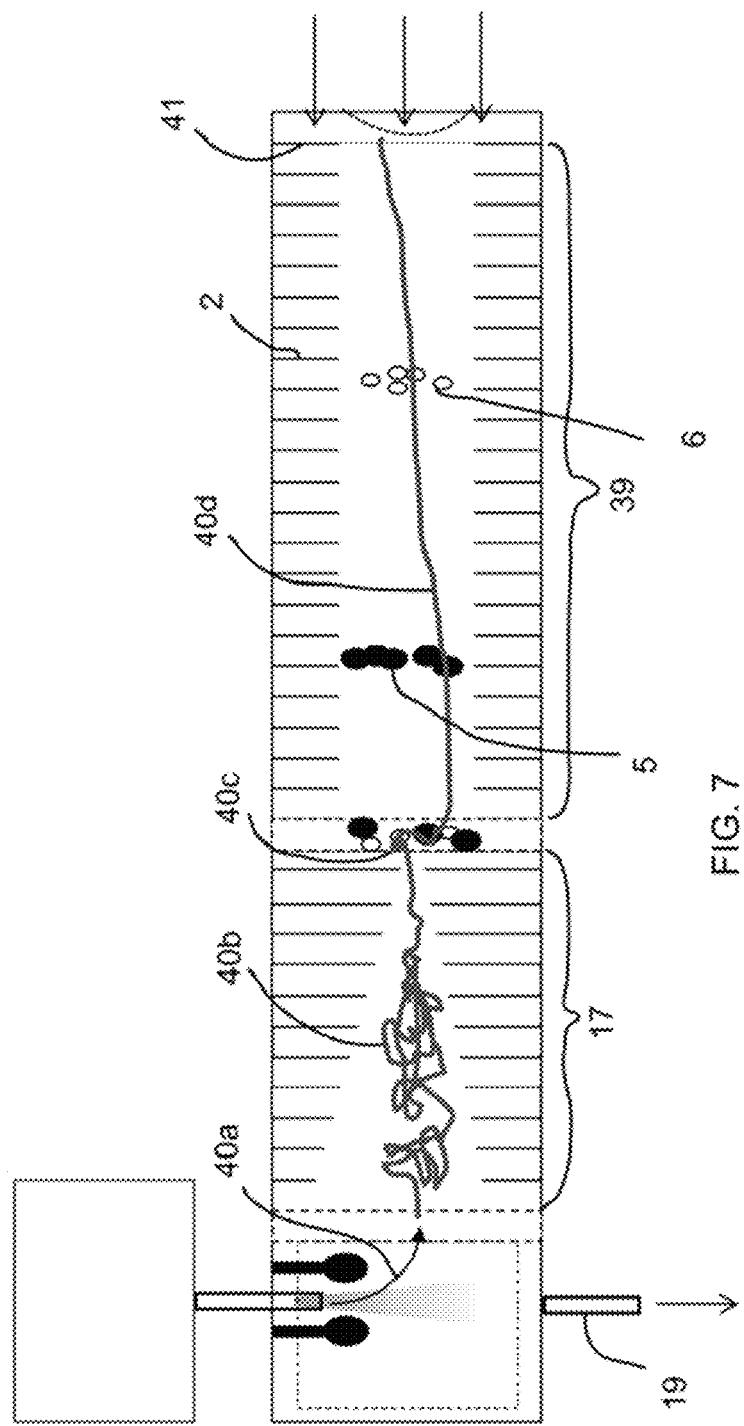
FIG. 7 illustrates a simplified ion trajectory that an ion may follow as it travels through yet another exemplary embodiment of the subject matter disclosed.

In order to illustrate the operation of the drift region, an exemplary ion trajectory is illustrated in FIG. 7 comprising a portion 40a in the first chamber, a portion 40b in the ion accumulation region, a portion in between two screens 40c and a portion 40d in the drift region. The hardware of FIG. 7 is the same as that of FIG. 2A. The portion 40a illustrates an ion trajectory influenced by a deflection voltage. The portion 40b, illustrates ion diffusion under the influence of trapping conditions. Portion 40c illustrates ion motion between two gate electrodes and the final portion 40d illustrates ion motion under the influence of an electric field in the drift region 39. In the drift region 39, ions are separated according to their electrical mobility by maintaining an electric field by use of a plurality of ring electrodes 2. After flowing through the drift region, the ions finally pass through a detector grid 41 before impacting the metal detector 54. In one embodiment the metal detector 54 is made of a sintered metal. The background gas enters through the metal detector 54 and a surrounding end plate 43, also made of sintered metal, which is electrically isolated from the detector 54. In another embodiment, the detector 54 and the surrounding end plate are not electrically isolated from each other.

The detector 54 is configured to measure the quantity of ions that travel from the electronic gate 37, 38 to the detector 54. Measurement of this rate along with knowledge of the distance between the electronic gate and the detector, gas pressure, gas velocity and electric field strength produces the desired signals that can be converted into the size and concentration of the ions being measured, as it will be further explained below. In addition, in some embodiments, numerical prediction of particle velocity using computational fluid dynamics and the measured time it takes the ions to flow from the electronic gate to the detector can be used to correct the effect of background gas velocity on the measurements of ion electrical mobility by use of an advantageous deconvolution technique.

Referring to FIG. 7, the sintered metal detector element 54 allows the background gas to flow uniformly into or out of the drift region by means of an end port 45 of the drift region. In one embodiment, the detector 54 and the surrounding end plate are formed into a rounded shape. In another embodiment, the detector 54 and the surrounding end plate are flat. One purpose of the shaped detector is to adjust ion flight times as influenced by the normal background gas parabolic velocity profile (110 in FIG. 27 and 120 in FIG. 28) resulting when gas flows through a tube, as explained below. One of the purposes of the grounded detector grid 41 is to minimize or eliminate the registering of a current signal at the detector 54 before the particles actually impact the detector. A cloud of ions approaching the detector presents to the detector a portion of its charge, known as an image charge, before ions actually strike the metal detector. The detector grid 41 blocks the image charge. The low pressure inside the drift region 39 is maintained by the application of a vacuum to the exit port 19.

Figure 8:
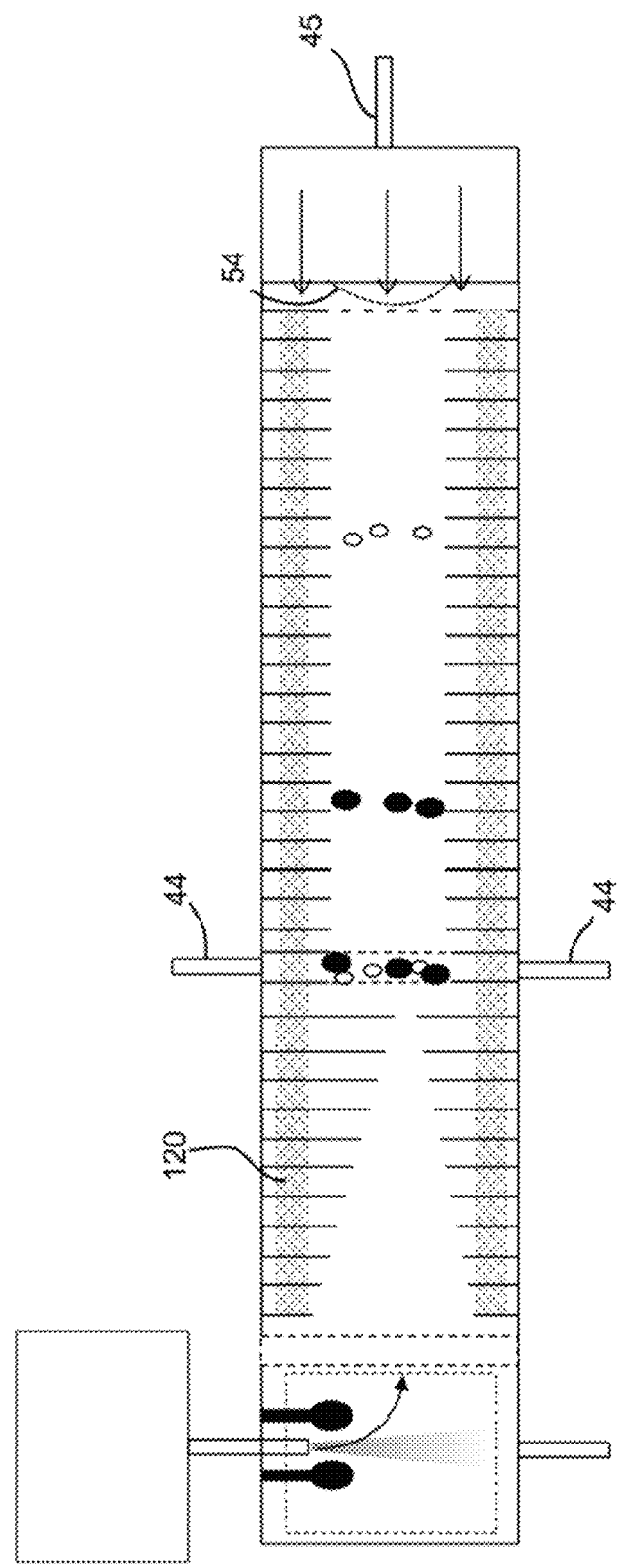
FIG. 8 illustrates yet another embodiment of the overall assembly of the subject matter disclosed.
Figure 9:
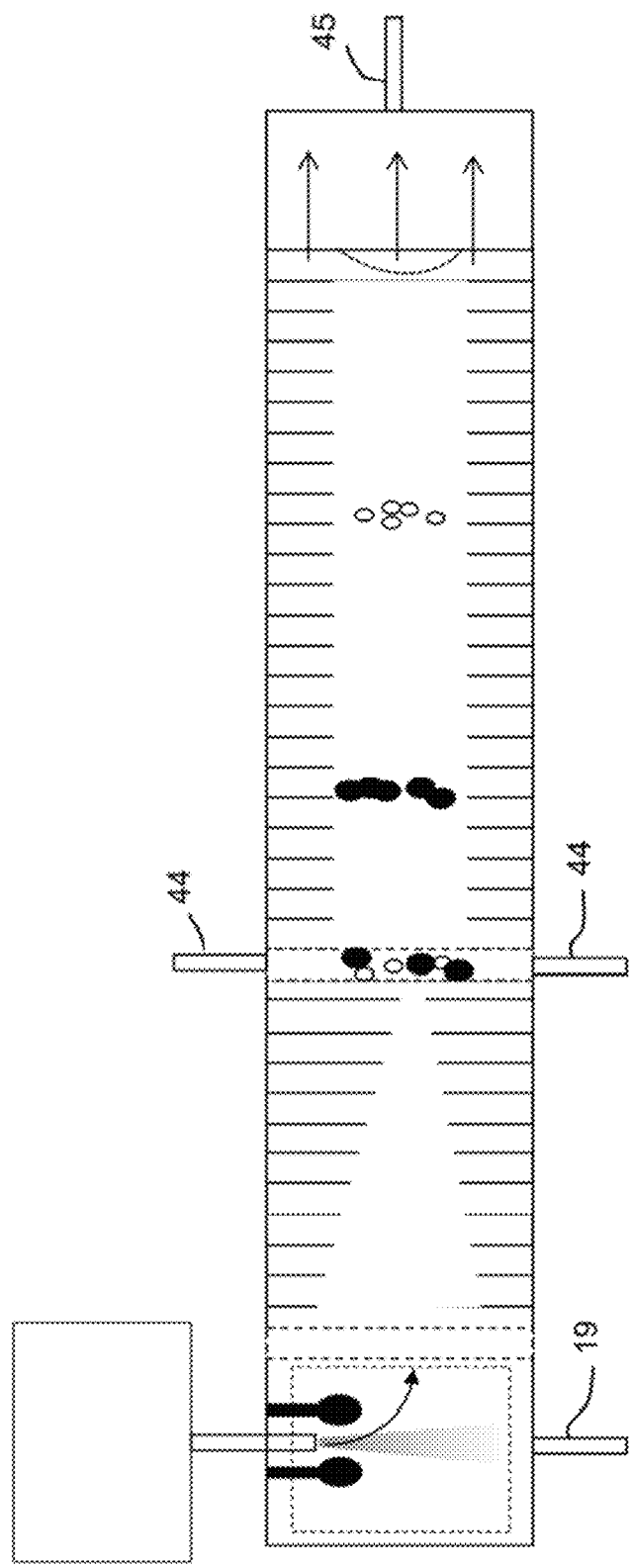
FIG. 9 illustrates as yet another embodiment of the overall assembly of the subject matter disclosed.

Another embodiment of the subject matter disclosed herein is illustrated in FIG. 8. An optional exhaust port 44 provides an alternative connection to a vacuum pump. This figure also shows dielectric material 120 between the ring electrodes of the accumulation region and the drift region. Another embodiment illustrated in FIG. 9 introduces background gas into port 44 and removes background gas by connecting port 19 and an exhaust port 45 dispensed on the exit end of the drift region to a vacuum pump.

In the drift region 39 ions are exposed to a fixed electric field generated by maintaining an approximately constant voltage drop between each equally-spaced ring electrode, thus the electric field is constant along the bore of the drift region. This means that regardless of where ions are located radially or longitudinally, they will experience a well-defined electric force that moves ions towards the detector. The profile 110 of the gas velocity illustrated in FIG. 26 in the drift region is not flat, an imperfection that contributes to a variation in ion velocity across the diameter of the drift region as illustrated by 110. The profile 110 describes an imaginary front surface on a plug of background gas as it travels towards the detector 54 (102). The gas velocity in the center of the drift region is higher than the gas velocity near the wall of the drift region and therefore the center portion of the gas plug has moved closer to the detector, after a time period (Δt) than the portion of gas that has traveled near the wall of the drift region. The lengths of the arrows that touch the profile 110 represent local gas velocity; the lengths being proportional to velocity. Knowledge of the background gas flow field, as obtained from CFD calculations, along with implementing a shaped detector 102', allows this variation to be remedied by means of mathematical algorithms, i.e., deconvolution of the arrival time distribution signal, as further explained below, and by means of altering the length of the flight trajectory by means of the shaped detector.

The use of a porous metal detector 102 (54) also provides a means to introduce a smooth flow of gas across the surface of the end plate on the drift region when gas is introduced into the drift region using port 45. Likewise, the illustration in FIG. 28 shows the use of a porous end plate as a means to introduce a flow of gas from the exit end of the drift region without disturbing the velocity profile of the gas in front of the detector because the porous material delivers gas at a constant velocity regardless of where the gas is moving through the porous material.

As ions are collected in the porous material of the disk, their charge is transferred to an ammeter. The varying intensity of the current signal is proportional to the varying flux of ions striking the detector. The ions have an arrival time distribution (a variation in the time required for an ion to travel from the entrance of the drift region to the detector) caused by their size distribution. Smaller ions arrive at the detector before larger ones. The temporal variation in the intensity of the detector signal can then be converted mathematically to a spectrum of ion size (cross-sectional area of an ion) using equations that are familiar to those knowledgeable with ion mobility. The disclosed instrument is designed to measure predominantly singly-charged ions so that the magnitude of the detector current at any specific drift time is proportional to the number of ions of a specific size. Basically, time slices in the observed time history of the signal observed at the detector can be converted to an ion size distribution. In the case for which the arrival time distribution is characterized with a single peak, an ion size can be calculated. In a second case when the arrival time distribution is characterized by multiple peaks, ion sizes can be reported for each peak. Indeed the final diameter of the drift region (e.g., a value around 7 cm for some embodiments) may be selected so as to maintain a low background flow velocity). Fourthly, the exit pressure of the drift region may be defined by a vacuum pump, which can readily achieve pressures below 0.01 atm in some embodiments, giving higher drift velocities and thus shorter analysis times. Vacuum pump operating pressures in the range from about 0.1 to about 0.0001 atm may be used in some applications. Fifthly, the overall length of the instrument (jet relaxation region 14 plus the ion accumulation region and the drift region 39 may be chosen to be about 30 cm and the flow tube diameter to be about 7 cm, thus resulting in transition of particles across the jet relaxation region in about 1 ms, with ion accumulation times extending to several hundred ms, while drift times may range in some embodiments from several to tens of ms.

Figure 10:
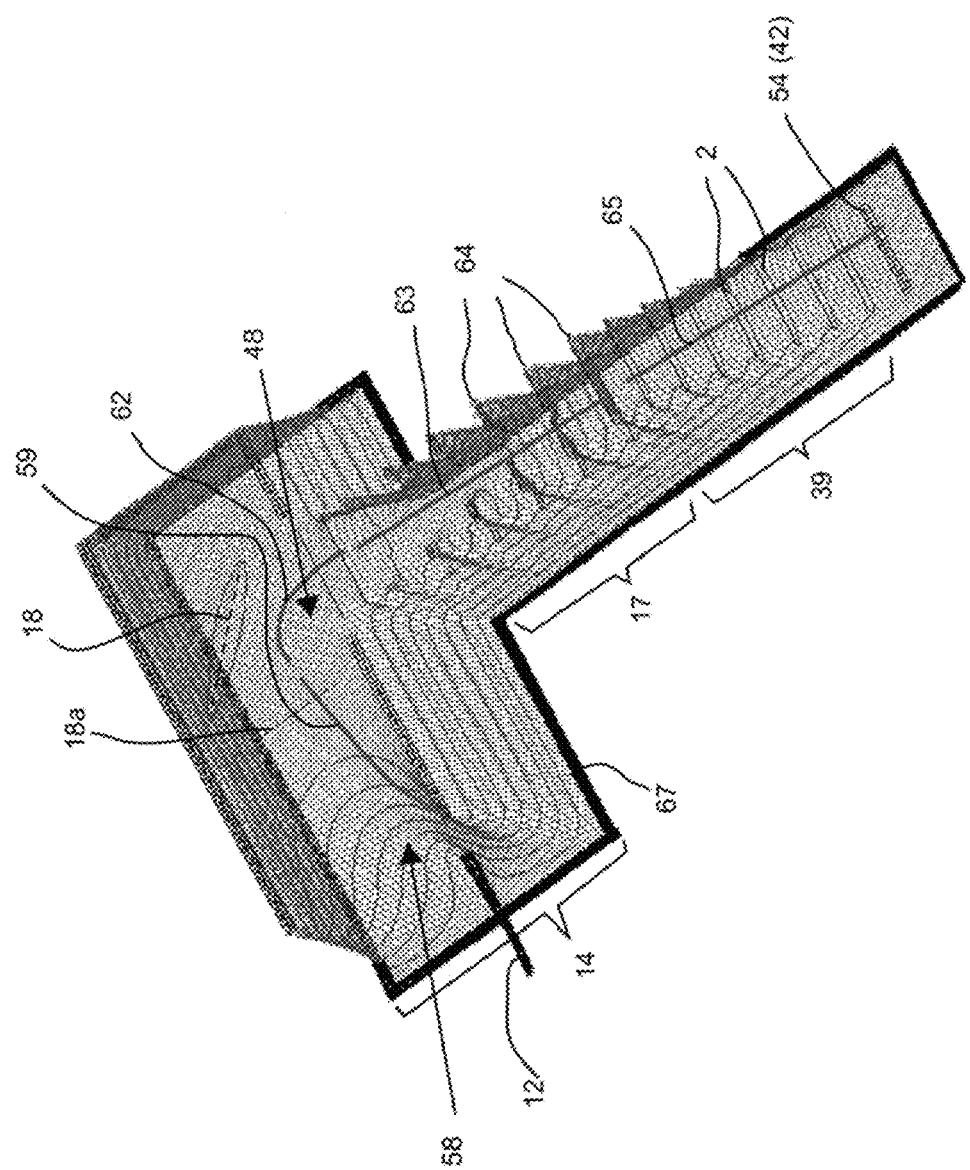
FIG. 10 illustrates an electrical potential energy surface for a fixed set of voltages applied to the electrodes in the subject matter disclosed.

An inlet nozzle 12 is used to introduce charged particles from an ion source, such as an electrospray source, into a jet relaxation region 14 internally surrounded with a wall electrode 14a disposed so as to prevent charged particles that are too small from flowing into the ion accumulation region 17. Around the nozzle 12 inlet location, there is an increase in the electric field intensity. By keeping the nozzle grounded, it is a feature of the disclosed material to control the size of ions that will actually enter the drift region from an ion source operated at ground potential. Those skilled in the art of transferring ions for one region of pressure to another region of reduced pressure may not appreciate from prior art the importance of jet velocity. A jet of gas propels ions along the course of the jet and can be used to overcome a resistance ions experience as they approach a potential wall such as a grid 18, illustrated in FIG. 10, inside the jet relaxation region 17 or the electrified wall of the jet relaxation region 14*a*. Such a condition of resistance occurs as ions exit the nozzle inside of a chamber whose wall is maintained at high voltage. On exit from the nozzle, ions experience the electric field imposed by the nozzle at ground potential and the wall maintained at high potential. If ion velocity is large enough, an ion will enter the chamber but if the velocity is low the electric field will force the ion to return to the nozzle 12. In FIG. 3, reference number 58 represents an electric barrier to the ions released from the nozzle. Depending on the magnitude of the electric field surrounding the nozzle, a fraction of small ions will be impeded by the electric barrier and turned to strike the nozzle. The electric field surrounding the nozzle is illustrated in FIG. 10. The shape of the electric field appears as an up-hill potential valley 58. The steepness of the valley is related to the difference in potential between the nozzle and the electrified wall of the jet relaxation chamber, along with the distance of the two parts. This up-potential feature excludes small charged ions from travelling towards the deflection screen 18. The steepness of the valley can be adjusted by moving the nozzle further into the walled chamber or further outward. In this manner, the steepness of the valley can be adjusted for the purpose of setting conditions that preclude ions of a certain size from travelling up the valley. All gas-borne particles that pass through the inlet nozzle experience a strong aerodynamic force—they are dragged by this force. Positively charged particles are subjected to a repulsive force created by the positive potential applied to the wall of the jet relaxation region 14 and voltage applied to the deflector screen 18 and or 18*a*. The aerodynamic force acts more strongly on large particles and pushes them up the potential valley. In so doing, it is possible to exclude small solvent ions from entering the ion accumulation region, and travelling further through the system where their large concentration could swamp the detector.

In order to simulate the motion of ions throughout the disclosed instrument, commercially available software, Simion, along with a modified Statistical Diffusion Simulation (SDS) Model was used to evaluate a number of different designs for the jet relaxation region, ion accumulation region, the drift region, gate electrodes and graphically plot ion trajectories, as shown above in FIG. 10 and later in FIGS. 14,15, 16 and 17B. Simion calculates the shape of the electric field around electrodes and the SDS Model calculates the motion of ions as they diffuse, or are dragged, through a reduced pressure gas under the influence of an electric field superimposed by Simion. The results of these calculations can be used to plot ion trajectories and reveal ion velocity at any location along an ion trajectory. The trajectories are useful for optimizing the performance of the various regions as one skilled in the art of ion optics may appreciate.

The motion of a single positive ion as it travels through the disclosed instrument is illustrated in FIG. 10 with a line segments representing its trajectory along the 3-D potential energy surface of the instrument. The potential energy floor 67, i.e., the ground plane, provides a base for the potential energy surfaces in the disclosed instrument, which are all portions of the instrument to which electrical power is applied. The height of the potential energy surface at any location is due to the magnitude of the local electric potential—a stronger (higher) local electric potential raises the local potential energy surface. The shape of the surface is a consequence of the voltage applied to the electrodes. An ion placed anywhere on the potential energy surface will tend to move downhill in static gas. The local gas velocity cannot be visualized in FIG. 10, but the consequence of the gas velocity on particle motion can be deduced from the shape of the potential energy surface and the path taken by an ion. A simple way to think of the potential energy surface is to consider the path of a golf ball on a putting green. An ion responds to the shape of the potential energy surface in the drift region, or for that matter, at any location inside the instrument disclosed herein, similarly to the way a golf ball moves on a putting green—it goes downhill and moves away from prominences.

The potential energy surface in FIG. 10 was designed to conduct particles through the disclosed device. An initial portion of an ion trajectory 59 represents an ion as it travels up the potential valley. The valley is steeper in a radial direction compared to an axial direction and provides a steering effect that guides the ions towards the center of the valley. A second portion 62 of the trajectory shows the ion responding to the voltage applied to the screen 18 which deflects the ion towards the entrance to the ion accumulation region 17. A third portion of the ion's trajectory 63 reveals a small imperceptible down-hill slope through a series of ring electrodes disposed in the ion accumulation region 17. In this illustration a first set of rings is powered with a higher voltage and a second set of ring electrodes is powered with a lower voltage. The illustration makes it appear that the ions are travelling through an open funnel where the wall of the funnel is corrugated 64. As the ion bumps up against the corrugations it is momentarily deflected towards the center of the passage. Eventually the ion trajectory leads to the end of the ion accumulation region 17, and a final portion 65 of the ion's trajectory represents the path of an ion as it travels downhill in the drift region 39 until its trajectory terminates at the ion detector 54 (42).

Figure 11:
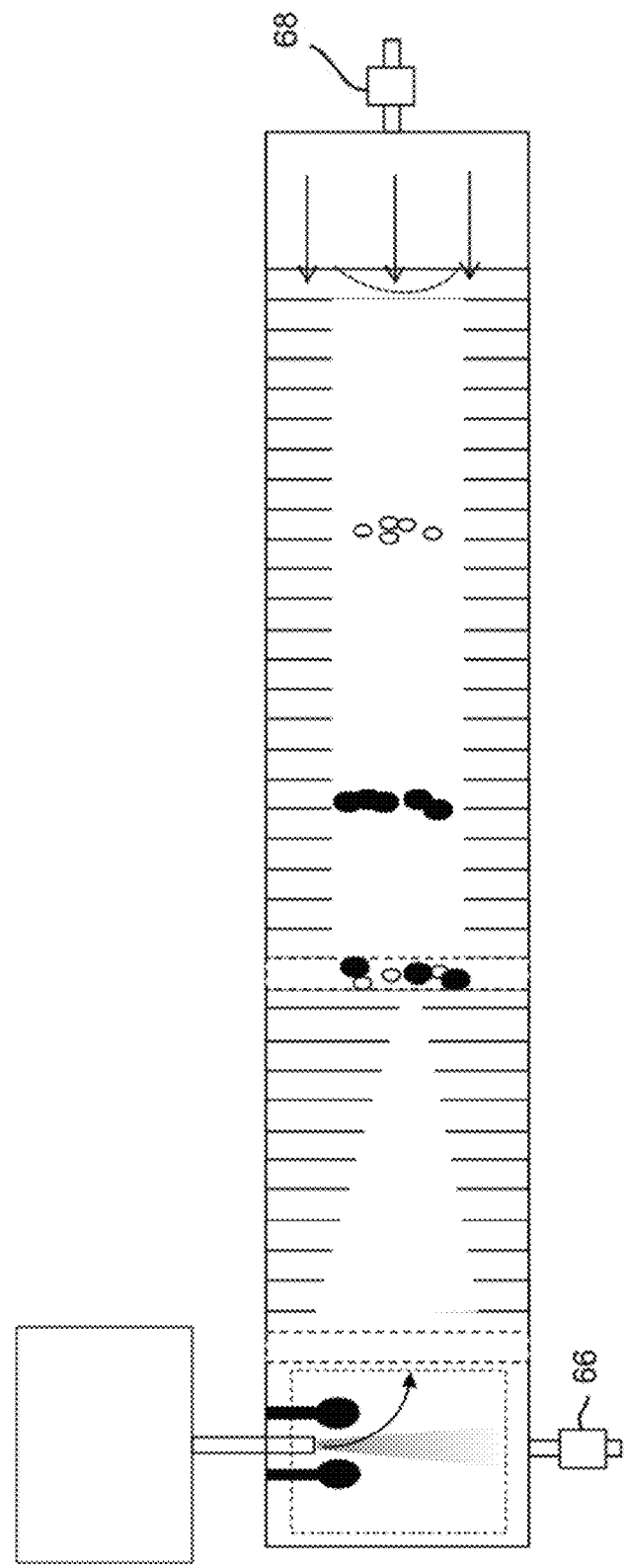
FIG. 11 illustrates as yet another embodiment of the overall assembly of the subject matter disclosed.
Figure 12:
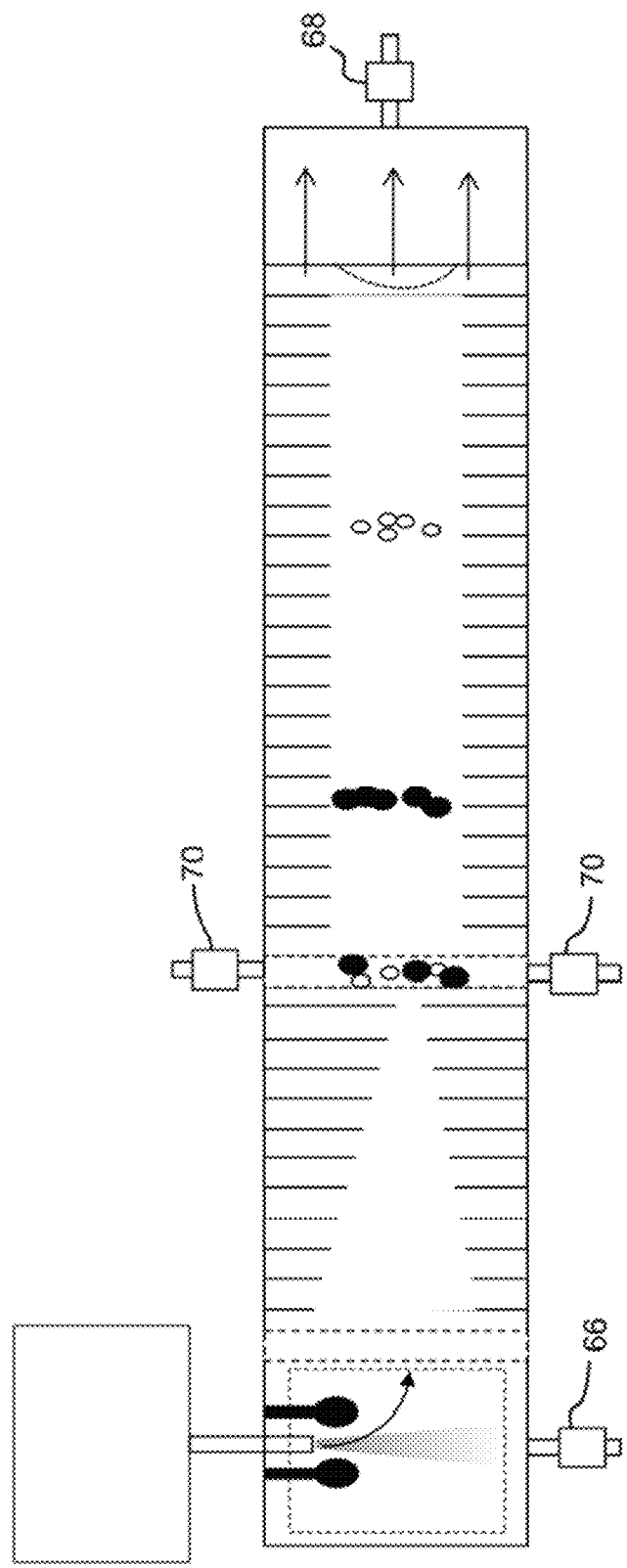
FIG. 12 illustrates as yet another embodiment of the overall assembly of the subject matter disclosed.
Figure 13:
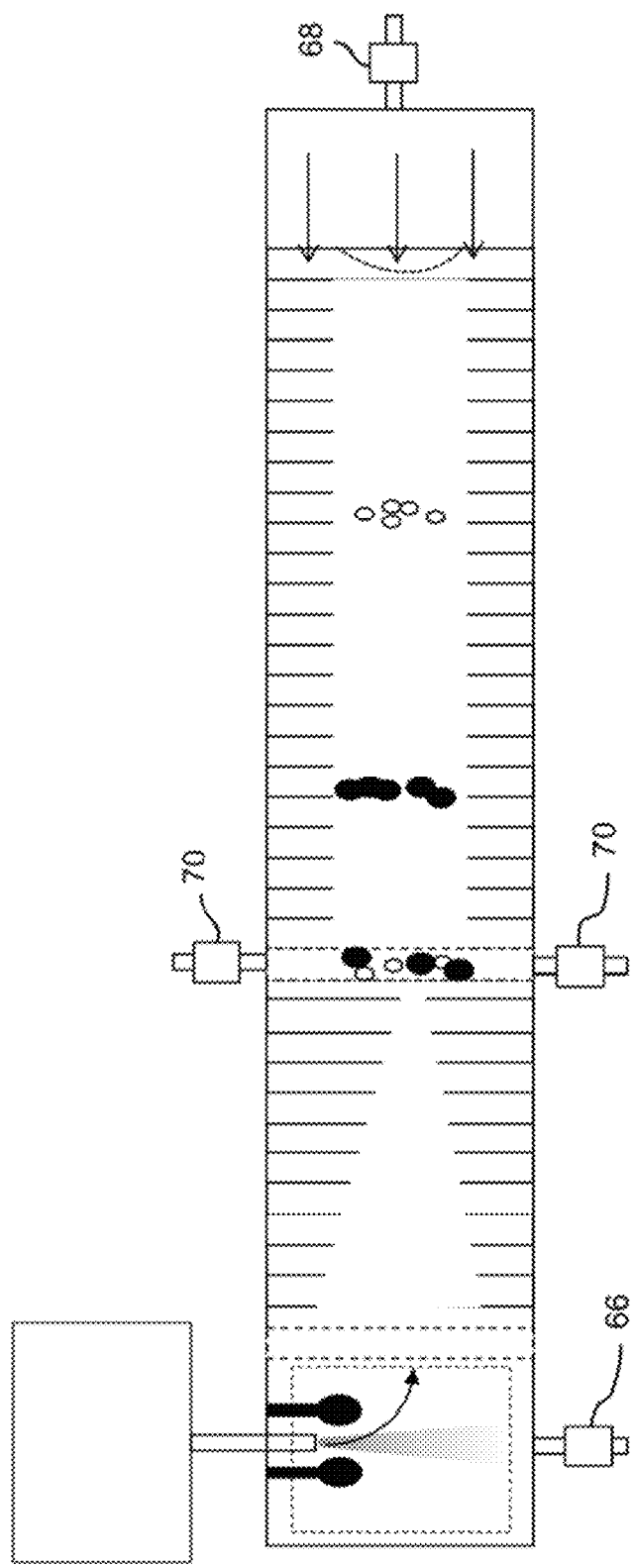
FIG. 13 illustrates as yet another embodiment of the overall assembly of the subject matter disclosed.

In another embodiment illustrated in FIG. 11, one or more valves 66 and 68 may also be provided to control the background gas flow during operation of the drift region 39. In operation, after ions accumulate in the gate region, the valves 66 and 68 are momentarily closed so as to stop the flow of background gas in order to minimize the effect of that variable on the measurement. After the measurement is finished, valves 66 and 68 are opened and the gas flow starts again. In another embodiment illustrated in FIG. 12, valves 66, 68, and 70 are operated to control the flow of gas. Valves 68 and 70 can be used to let gas into the instrument while valve 66 provides a way to remove gas from the disclosed instrument. In yet another embodiment illustrated in FIG. 13, gas is removed through valves 66 and 70 while valve 68 allows gas to enter the exit 45 to the drift region. In operation, after the ion accumulation region is appropriately filled with ions, the valves can be closed so that the drift region can be operated with static gas—no flow, while maintaining particles in the trap. Then the trapped particles may be released into a stagnant gas. This will increase performance because any influence of gas eddies or gas velocity will be removed. In another embodiment, it is also possible to trap charged particles in the electronic gate and then introduce a countercurrent flow of clean gas from the exit end, so as to flush out solvent vapors that were carried initially into the drift region along with ions before making the measurements. In some embodiments the valves are electric valves. The timing of the operation of these valves may be varied to accomplish the described effect on the background gas flow.

One parameter of importance in choosing voltages applied to electrodes in the disclosed instrument is the Paschen limit for corona discharge, which must be avoided.

The Paschen limit predicts an upper limit for establishing an electric field without electrical discharge for a range of operating pressures. The selection of voltage parameters for the gate and drift region are chosen so as not to exceed the Paschen limit. Those skilled in the art will appreciate there is a desire to operate with voltages as high as is possible because high voltage provides conditions conducive to optimal resolution.

Figure 14:
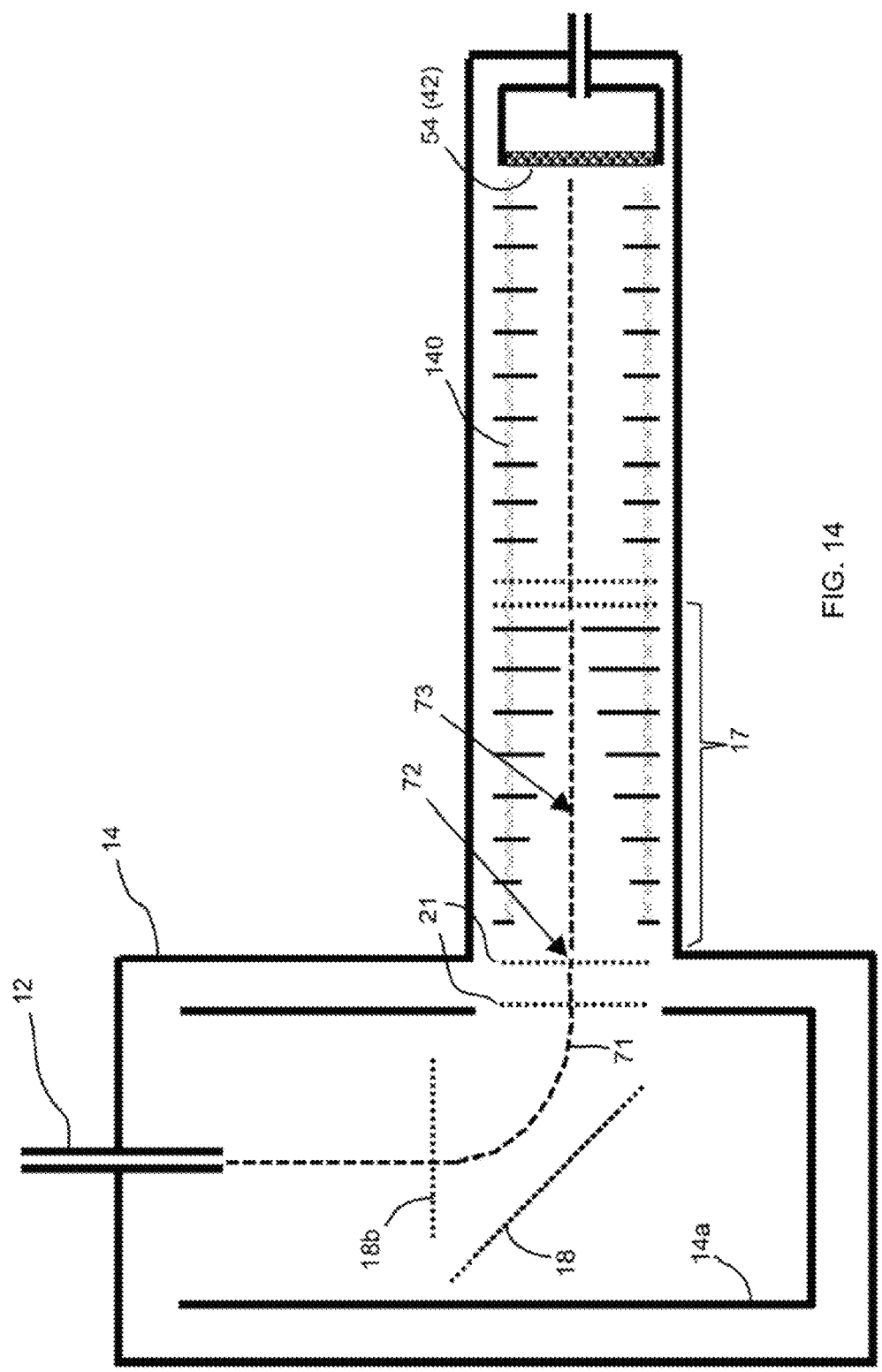
FIG. 14 illustrates ion trajectory representing the path followed by an ion in the subject matter disclosed.

As illustrated in FIG. 14, the result of a Simion simulation along with the use of a SDS model, ions travel along a trajectory represented by a line 71. Ions start their trajectory in a jet of gas 13 (FIG. 2A), then are deflected out of the jet and into the ion accumulation region 17 by responding to a voltage applied to screen 18. Voltage applied to screen 18 presents a potential ridge 83 to ions travelling in trajectory 71 causing them to divert orthogonally, and after passing through grids 21, travel into the entrance 72 of the ion accumulation region 17. After passing through the entrance 72 to the ion accumulation, the ions may become trapped in the interior 73 of the ion accumulation region 17 where they are captured by a depression in the local electric field. The depression in the local electric field, not visible in FIG. 14, acts like a bowl in which there is a marble, captures ions and prevents them from travelling elsewhere. Diffusion jostles the ions while they are confined in the depression. Further description of ion motion in the disclosed material provides information about the efficiency with which ions can be trapped. Features of the ion accumulation region such as the internal diameter of the funnel, voltages, both DC and pulsed, which are applied to the ring electrodes in the funnel, gas pressure, ion mass, ion charge affect ion motion. The figure also illustrates dielectric material 140 between the electrodes and further includes a porous detector 54 (42, 102).

Figure 15:
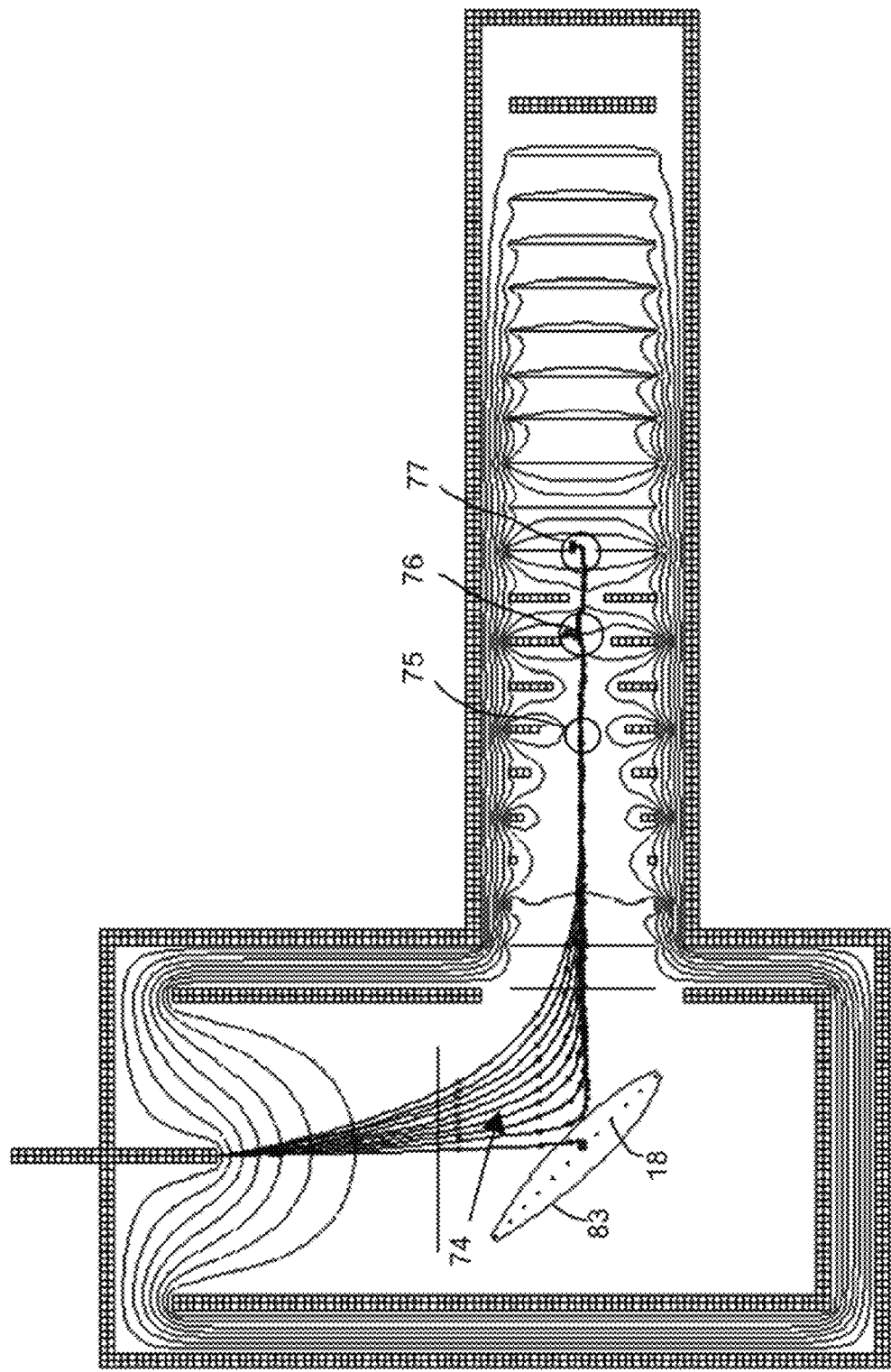
FIG. 15 illustrates electrical field intensity along with a plurality of ion trajectories representing paths followed by ions travelling through the subject matter disclosed.

FIG. 15 further illustrates the deflection of ions away from the centerline of a gas jet where it can be understood that not all ions exiting the nozzle 12 travel along the centerline of the nozzle and that a portion of the ions escape the nozzle 12 with trajectories 74 diverging from the centerline. The voltage applied to the deflection screen 18 guides all ions within +/−45 deg of the nozzle's centerline to turn into the ion accumulation region. This illustration exemplifies how ions generated in an ion source at atmospheric pressure, transit through a nozzle, become dragged by the jet of gas emanating from the nozzle and enter the ion accumulation region after being deflected by the voltage applied to a deflecting screen 18. Appropriate choice of the voltages applied to the ring electrodes in the ion accumulation region, provides a means to capture, i.e., trap, ions along the longitudinal axis of the ion accumulation region. Ions were trapped in areas designated by circles 75, 76, and 77. The circles designate approximate regions where the local electric field is bowl-shaped and capable of trapping ions. Circles 75, 76, and 77 mark locations where ions were trapped during simulations performed with Simion software. These circles are not limiting and other regions within the ion accumulation region, which are not encircled, also effectively trap ions.

Exemplary voltages applied to one embodiment of the disclosed material (see FIG. 4) applies pulsed voltage to a first set of electrodes 29 while the second set of electrodes 30 is grounded and then the pulsed voltage is applied to electrodes 30 whiled the electrodes 29 are grounded. See FIG. 5. The pulsed voltage applied to each set has the same magnitude and values between 50 and 1000 volts may be used. In one embodiment, the voltage is 200 but operation of the disclosed material is not limited to this value.

After a period of time, the first set is grounded electrically and the second set is powered. In this fashion, a pulse of power is applied to the set one and later to the second set repeatedly during the duration of the ion accumulation time. In a further embodiment, pulsed power is repeatedly applied to one set of electrodes, either 29 or 30, and the other set is grounded continuously. It should be further understood that the pulsed power, whether RF or pulses as shown in FIG. 5, may be switched off at any moment either to help release ions from the ion accumulation region or to minimize the effect of pulsed power on the response of the detector. It is known to practitioners in the art of analog signal processing that pulsed power can interfere with detector signals of the type registered by the detector in the disclosed material and impose a noisy background signal on the ion signal. Minimizing the background detector signal by turning off the pulsed power during measurements of ion arrival time distributions is a feature of the disclosed material.

Figure 16:
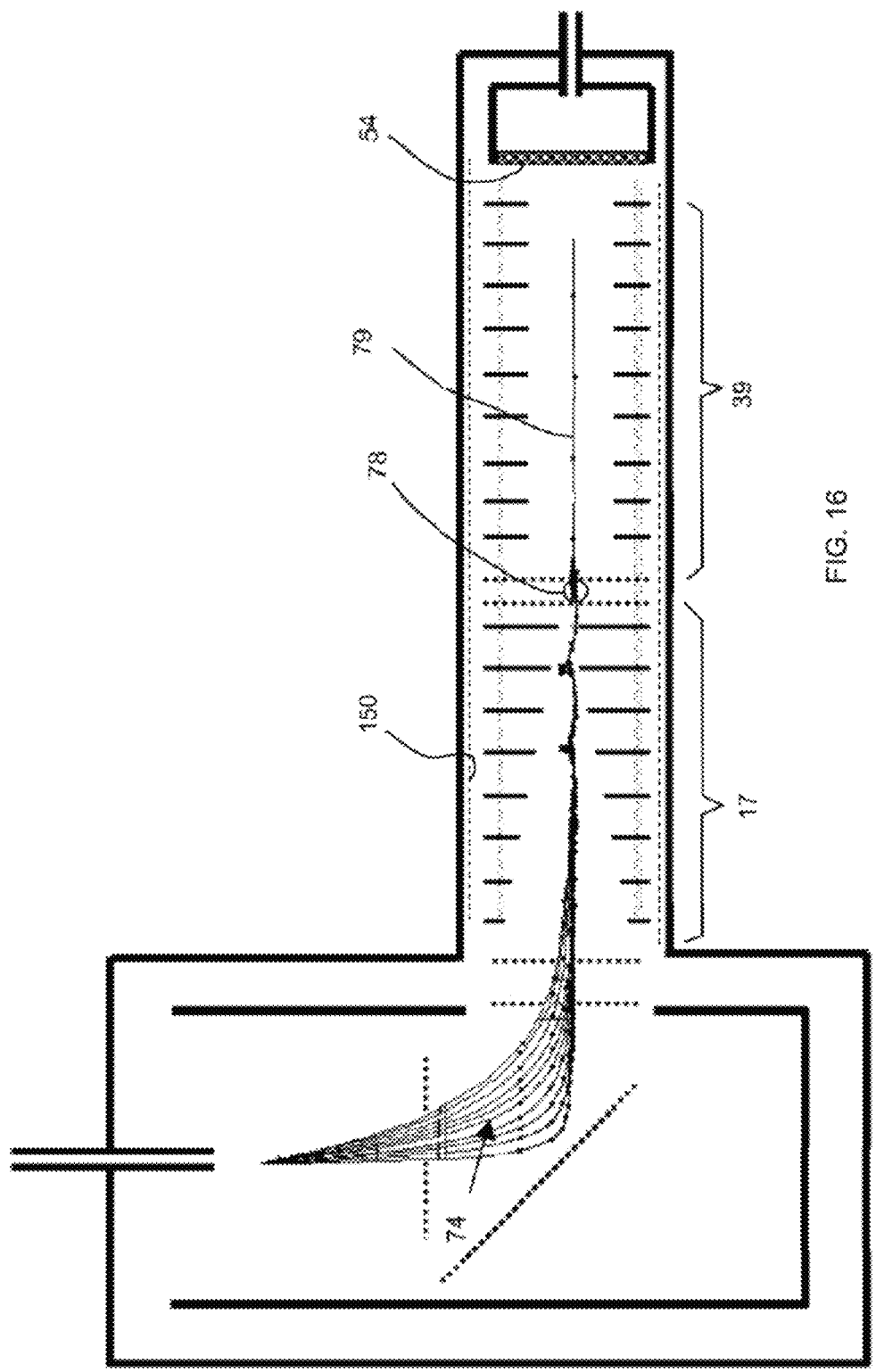
FIG. 16 illustrates a plurality of ion trajectories, similar to what is illustrated in FIG. 15, but with the addition of trajectories of ions following their release from trapping region between grids 78 and their travel to a detector 54.

FIG. 16 further illustrates the motion of ions in the disclosed instrument. The circle 78 encompasses a small region between grids 37 and 38 where ions were trapped after they were released from the ion accumulation region 17. Grids 37 and 38 comprise an electronic gate. By proper manipulation of voltages applied to the ring electrodes in the ion accumulation region 17 and grids 37 and 38, ions can be guided out of the ion accumulation region and into the region between grids 37 and 38, where they can be trapped for a second period of time, the first period of time being the time they were trapped in the ion accumulation region. Then by proper choice of voltages applied to grids 37 and 38, the ions can be released into the drift region, where they are shown to follow a trajectory 79 that terminates at the ion detector 42 (54). Exemplary voltages applied to the ring electrodes in the drift region are a few hundred to a maximum of 10,000 volts distributed across the voltage divider network shown in FIG. 6. It is to be understood that higher positive voltage is applied to the portion of the divider network that is proximal to the electronic gate and that lower voltage, even zero volts, may be applied to the detector grid 41. Any selection of voltage that provides 1 V/cm to as much as 1000 V/cm is within the operating range of a drift region, recognizing that the Paschen limit will impose an upper operating electric field limit. A preferred operating condition is to apply voltage to the divide network so as to create a uniform electric field of 100 V/cm across the length of the drift region. FIG. 16 illustrates an embodiment having an inner lining 150 that surrounds the exit to the jet relaxation region, the ion accumulation module and/or the drift tube to provide a means to establish an electrical shield around these components. The lining can be connected to a power supply to establish an electric field that reduces the local electric field strength for the purpose of minimizing electrical discharge. In one embodiment the shield is provided with a voltage that is between zero and the highest potent applied to the shielded components.

Figure 17B:
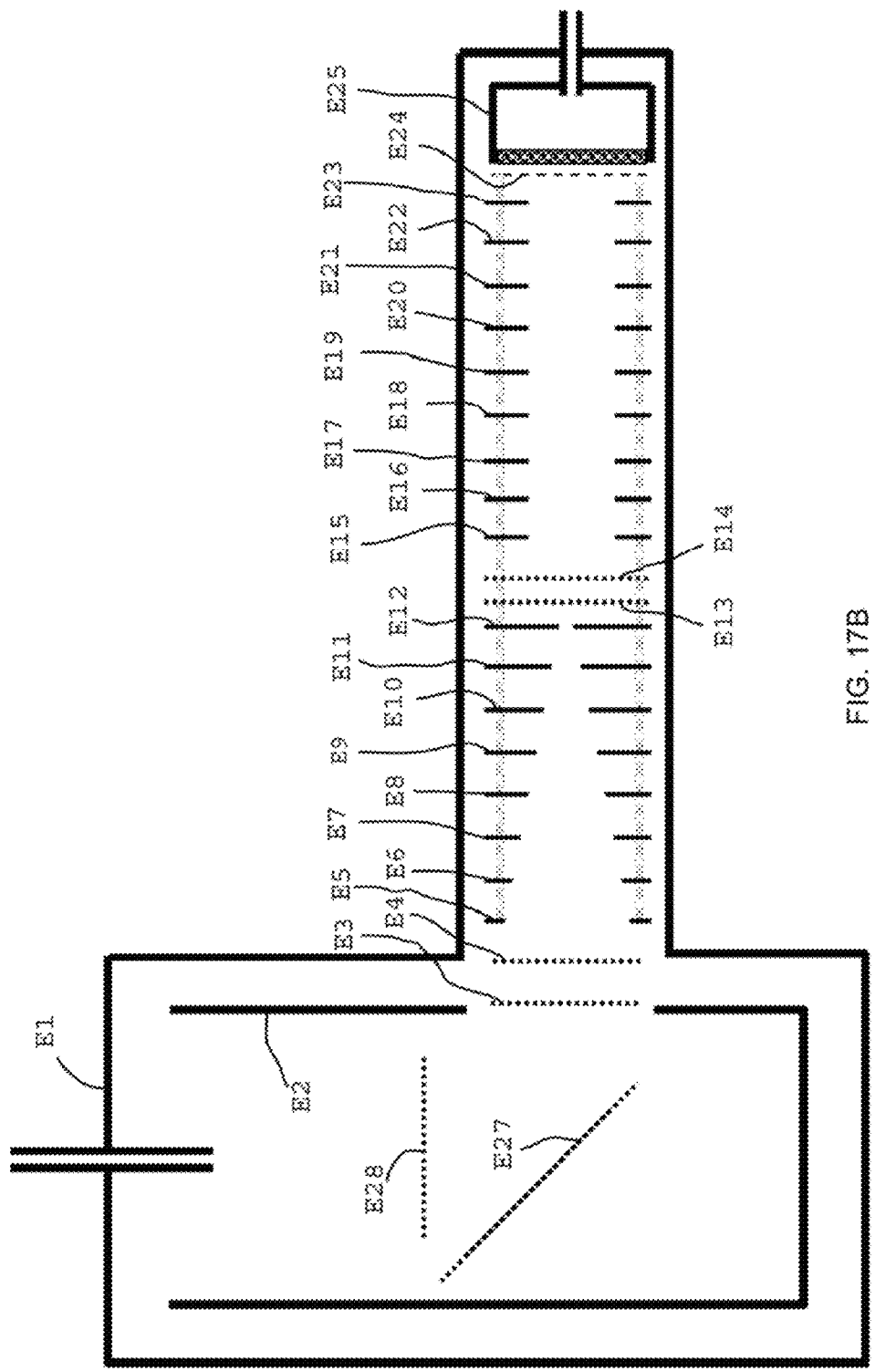
FIG. 17B shows the assignment of numbers to the electrodes in the instrument shown in FIG. 17A.

FIG. 17A presents exemplary voltages applied to the electrodes during the calculation of Simion simulations presented as illustrations in FIGS. 14-16. The numbers in the table preceded by a colon represent electrodes in the disclosed information—#1 is assigned to electrode #1. The assignment of numbers to the electrodes in the instrument is presented in FIG. 17B. The electric field intensity depends on the values listed in the table in FIG. 17A. The data in this table established the voltage applied to electrodes and the resulting electric field intensities illustrated in FIG. 10 and FIGS. 14-16.

FIG. 17C shows an embodiment of the ion accumulation region of FIG. 17B. In this embodiment, the edge 80 of the inner opening of the ring electrodes is fabricated with a step detail as illustrated in the enlarged drawing of FIG. 17D. The step along the inner opening provides a means to control the electric field near the edge of the inner opening which improves ion trapping efficiency. Curved lines drawn around electrodes (patterned rectangles represent ring electrodes) reveal the shape of the electric field nearby the electrode. Near to electrodes distinguished with solid arrows the shape of the electric field can be seen to bend towards the entrance (left side) of the ion accumulation region. The single ring electrode distinguished with a dashed arrow illustrates the electric field near to the inner rim of an electrode with a step in the rim. The electric field line near the step does not bend towards the opening to the ion accumulation region and instead is symmetrically centered around the electrode. The shape of the electric field near the inner rim of an electrode influences ion trajectories. Ion trajectories illustrated with solid arrows show trajectories that terminate on an electrode surface. This results because the bend in the electric field guides ions towards an electrode. Ion trajectories illustrated with dashed arrows show trajectories that turn towards the longitudinal axis of the ion accumulation region, an effect that steers ions away from the inner rim of a ring electrode and results in improved ion trapping.

Figures 18A, 18B:
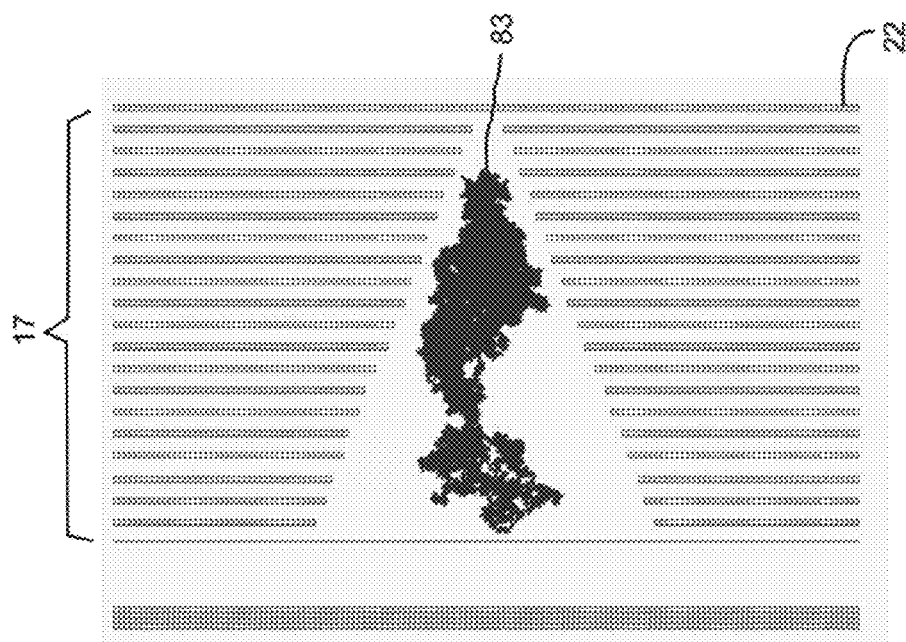
FIG. 18A illustrates the trajectory of a $10^4$ Da ion as it traveled in the ion accumulation region under a set of electrical and gas conditions presented in the accompanying table of FIG. 18B.

FIG. 18A is an illustration of a Simion simulation of the trapping of an ion in the accumulation region 17. The wide vertical lines represent the ring electrodes 22 in the ion accumulation region 17. The pattern 83, a wandering line inside of the ion accumulation region 17 illustrates the trajectory of a singly-charged $10^4$ Da ion as it travels under the influence of power applied to the ring electrodes in the ion accumulation region 17. The wandering line represents a 100 ms time course of the ion. Its trajectory courses over itself repeatedly, thus obscuring early portions of its trajectory. FIG. 18B is a table showing a summary of conditions that were used to generate the simulated trajectory. Those knowledgeable of Simion simulations will recognize the constraints imposed with the conditions listed in FIG. 18B.

Figures 19A, 19B:
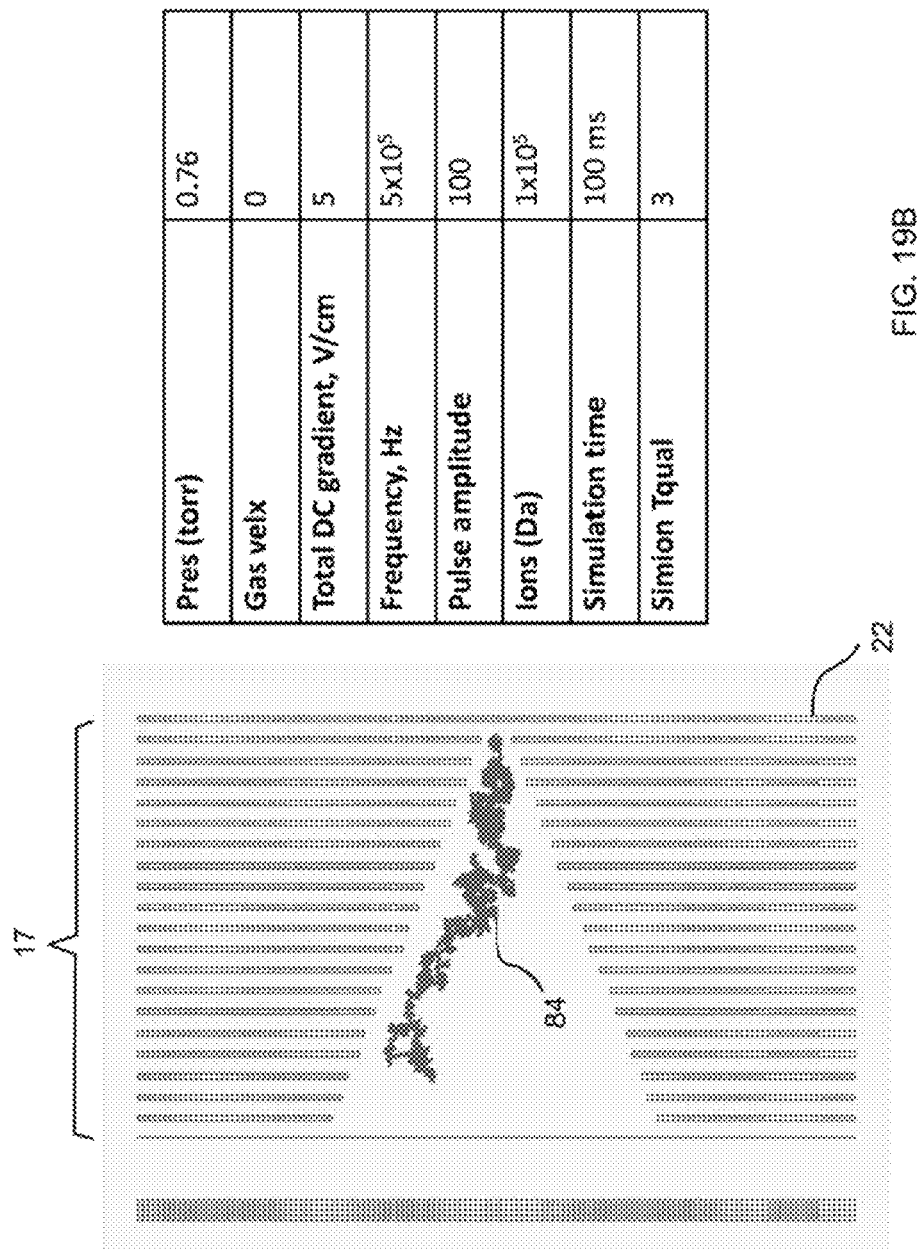
FIG. 19A illustrates the trajectory of a $10^5$ Da ion as it traveled in the ion accumulation region under a set of electrical and gas conditions presented in the accompanying table of FIG. 19B.

FIG. 19A is an illustration of a Simion simulation of the trapping of an ion in the accumulation region 17. The wide vertical lines represent the ring electrodes 22 in the ion accumulation region 17. The pattern 84, a wandering line inside of the ion accumulation region 17 illustrates the trajectory of a singly-charged $10^5$ Da ion as it travels under the influence of power applied to the ring electrodes in the ion accumulation region 17. The wandering line represents a 100 ms time course of the ion. Its trajectory courses over itself repeatedly, thus obscuring early portions of its trajectory. The trajectory represents a 100 ms time course. FIG. 19B is a table showing a summary of conditions that were used to generate the simulated trajectory. Those knowledgeable of Simion simulations will recognize the constraints imposed with the conditions listed in FIG. 19B.

Figures 20A, 20B:
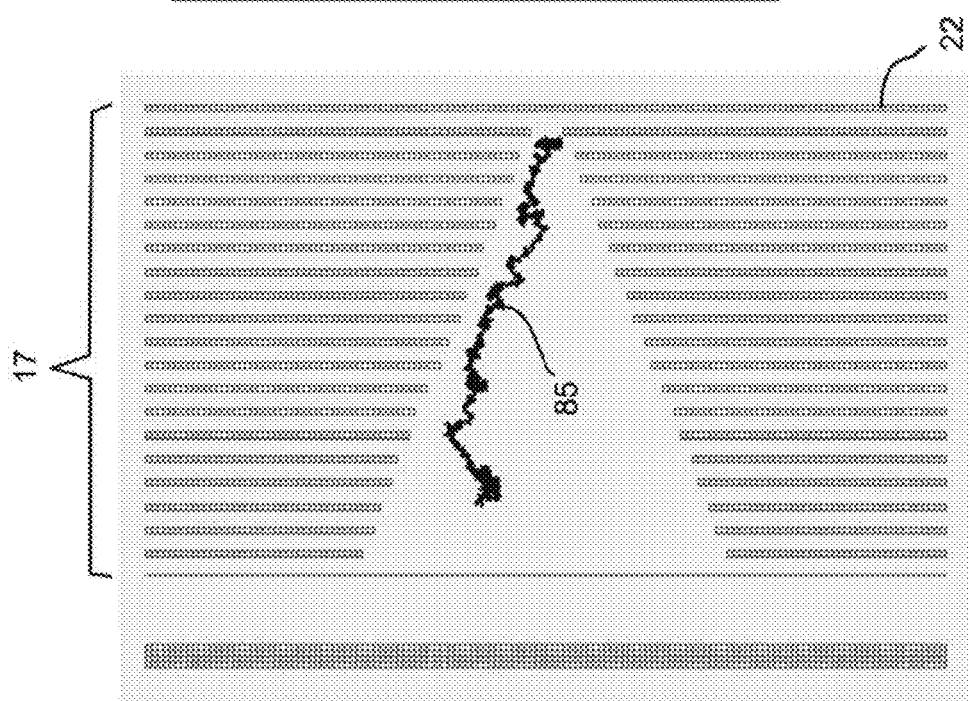
FIG. 20A illustrates the trajectory of a $10^6$ Da ion as it traveled in the ion accumulation region under a set of electrical and gas conditions presented in the accompanying table of FIG. 20B.

FIG. 20A is an illustration of a Simion simulation of the trapping of an ion in the accumulation region 17. The wide vertical lines represent the ring electrodes 22 in the ion accumulation region 17. The pattern 85, a wandering line inside of the ion accumulation region 17 illustrates the trajectory of a singly-charged $10^6$ Da ion as it travels under the influence of power applied to the ring electrodes in the ion accumulation region 17. The wandering line represents a 100 ms time course of the ion. Its trajectory courses over itself repeatedly, thus obscuring early portions of its trajectory. This line, i.e., a trajectory, was calculated using Simion. The trajectory represents a 100 ms time course. FIG. 20B is a table showing a summary of conditions that were used to generate the simulated trajectory. Those knowledgeable of Simion simulations will recognize the constraints imposed with the conditions listed in FIG. 20B.

Figure 21:
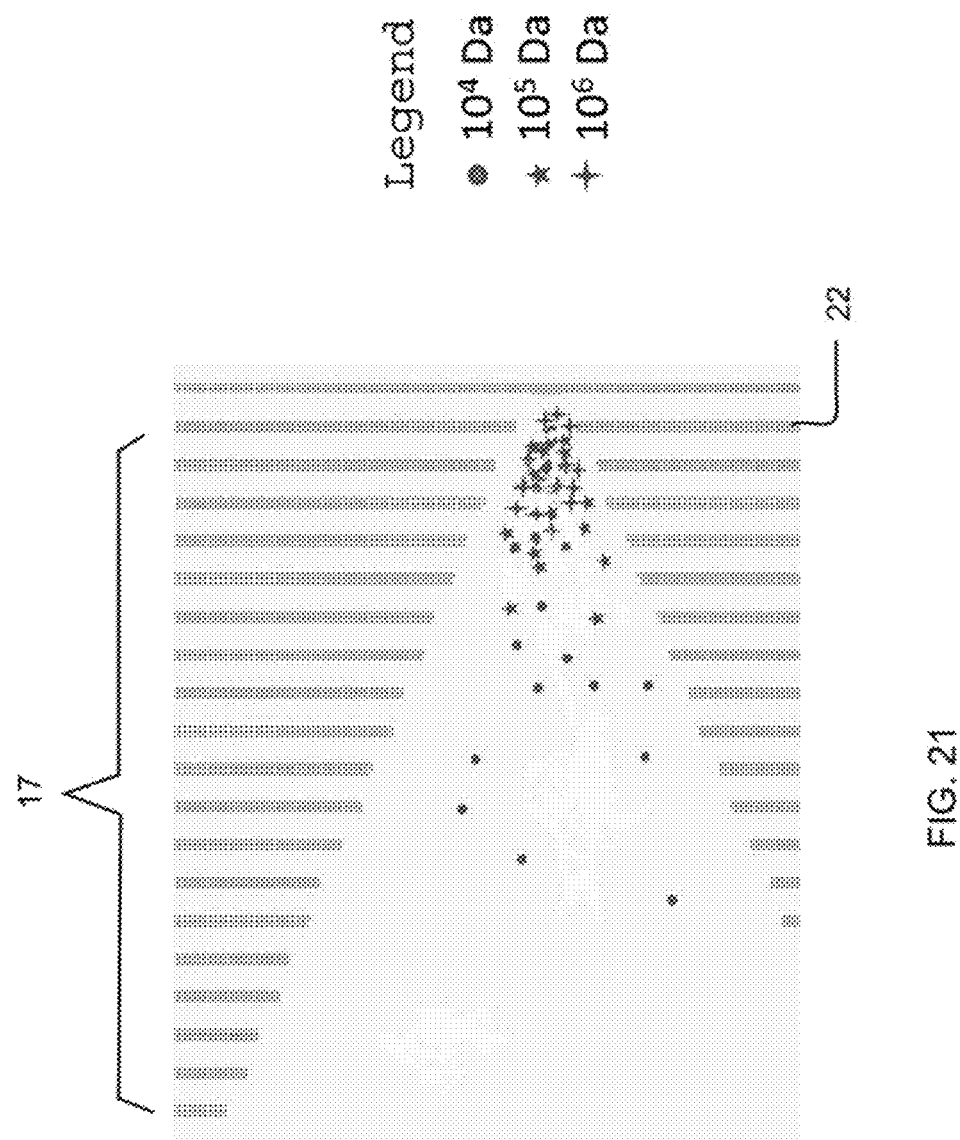
FIG. 21 illustrates the location of multiple numbers of $10^4$, $10^5$, and $10^6$ Da ions at the end of a 50 ms trapping time, i.e., after they have moved around in the ion accumulation region for 50 ms.

FIG. 21 is an illustration of a Simion simulation of the accumulation of ions in the accumulation region 17. The wide vertical lines represent the ring electrodes 22 in the ion accumulation region 17. The dots, stars and crosses represent the location in the accumulation region 17 of singly-charged ions of mass $10^4$, $10^5$ and $10^6$ Da (ten ions of each mass) at the end of a 100 ms simulation time. The increased density of data points in the narrow exit of the ion accumulation region 17 can be understood to demonstrate that ions accumulate near the exit end of the accumulation region 17. FIG. 21B defines the mass of ions represented in FIG. 21A by dots, plus signs and star symbols.

Figure 22A:
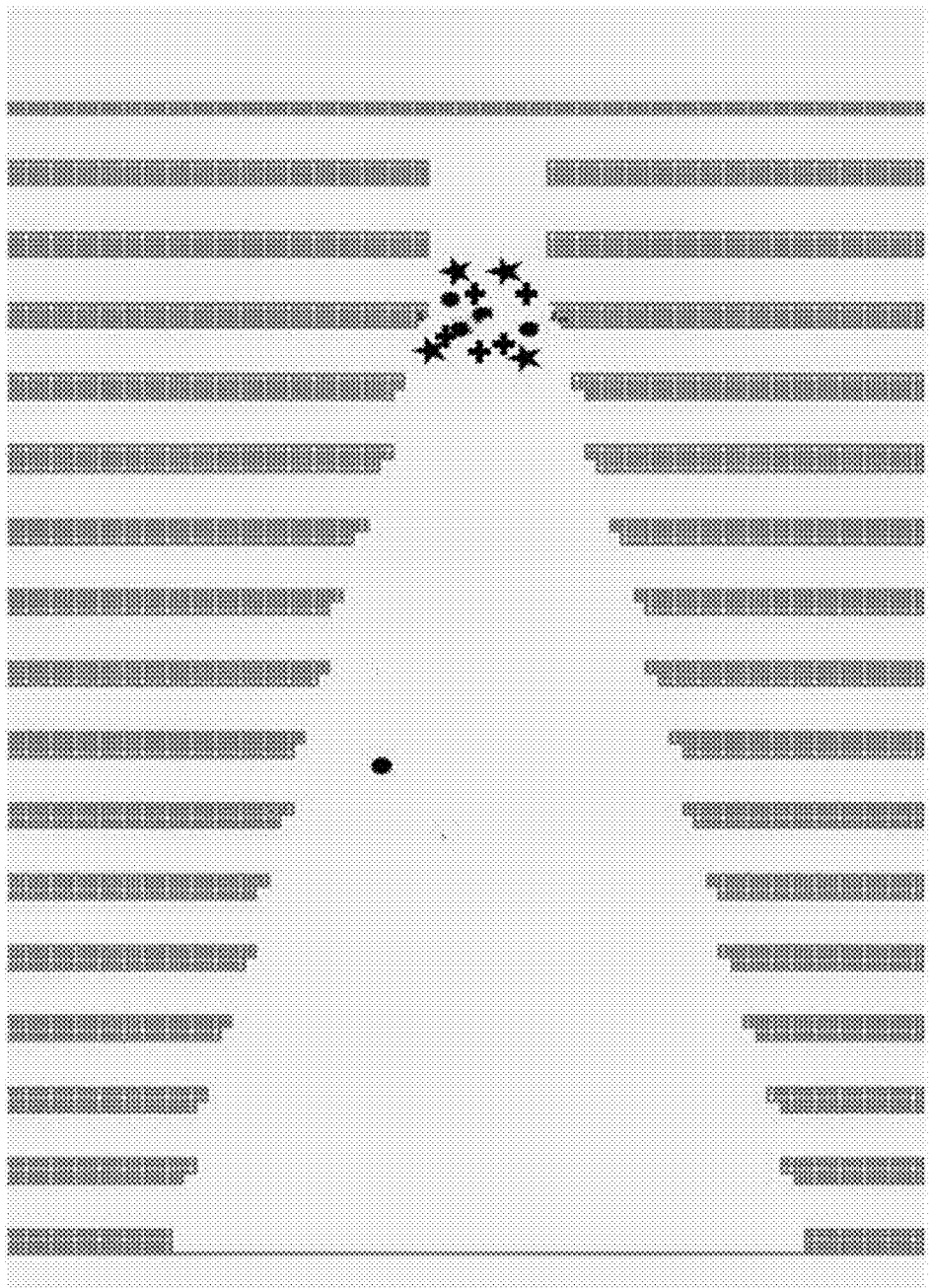
FIG. 22A is an illustration of a Simion simulation of the accumulation of ions in the accumulation region.
Figure 22C:
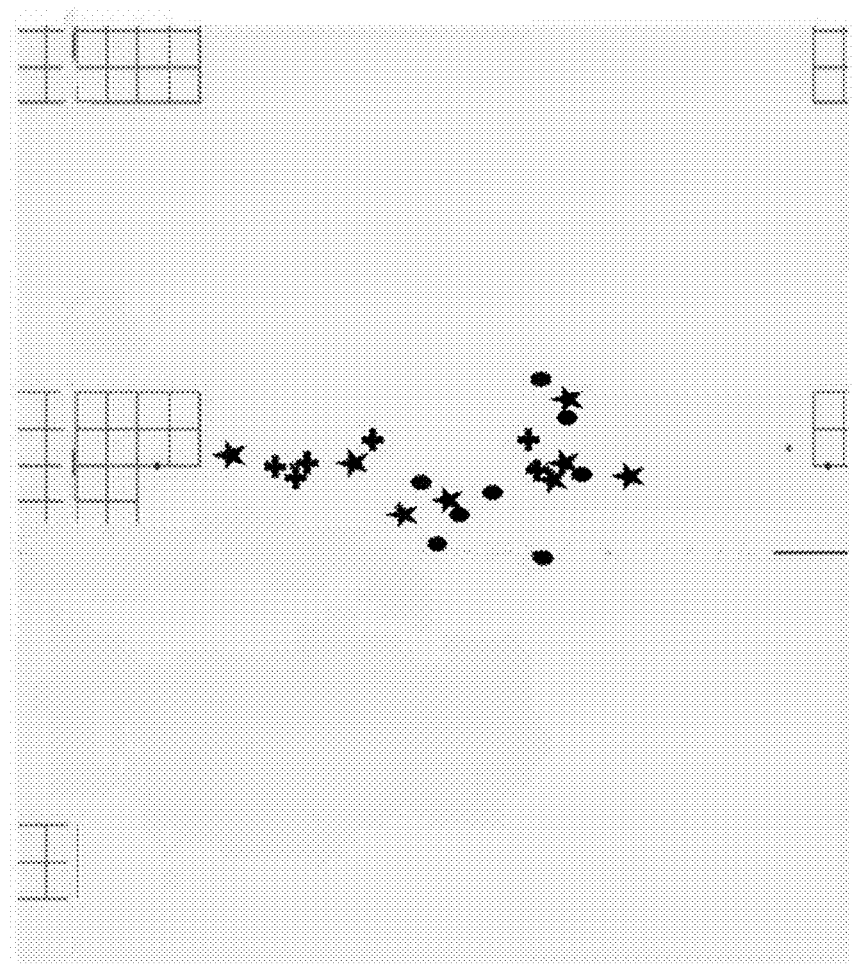
FIG. 22C is an enlarged view of the exit end of the ion accumulation region presented in FIG. 22A.

FIG. 22A is an illustration of a Simion simulation of the accumulation of ions in the accumulation region 17. The wide vertical lines represent the ring electrodes 22 in the ion accumulation region 17. This figure shows an alternative design for the exit end of the accumulation region 17. When FIG. 22A is compared to FIGS. 18A, 19A, 20A and 21A, it can be seen that the exit end of the ion accumulation region appears as a cylindrical tube in cross-sectional representation. The dots, stars and crosses represent the location in the accumulation region 17 of singly-charged ions of mass $10^4$, $10^5$ and $10^6$ Da (ten ions of each mass) at the end of a 100 ms simulation time. This figure uses the same legend as in FIG. 21. The increased density of data points in the narrow exit of the ion accumulation region 17 can be understood to demonstrate that ions accumulate near the exit end of the accumulation region 17. It can also be understood that the tube shape of the exit end alters the location where ions accumulate. FIG. 22B is a table showing a summary of conditions that were used to generate the simulated trajectory. Those knowledgeable of Simion simulations will recognize the constraints imposed with the conditions listed in FIG. 22B. FIG. 22C is an enlarged view of the exit end of the ion accumulation region presented in FIG. 22A.

Figure 23A:
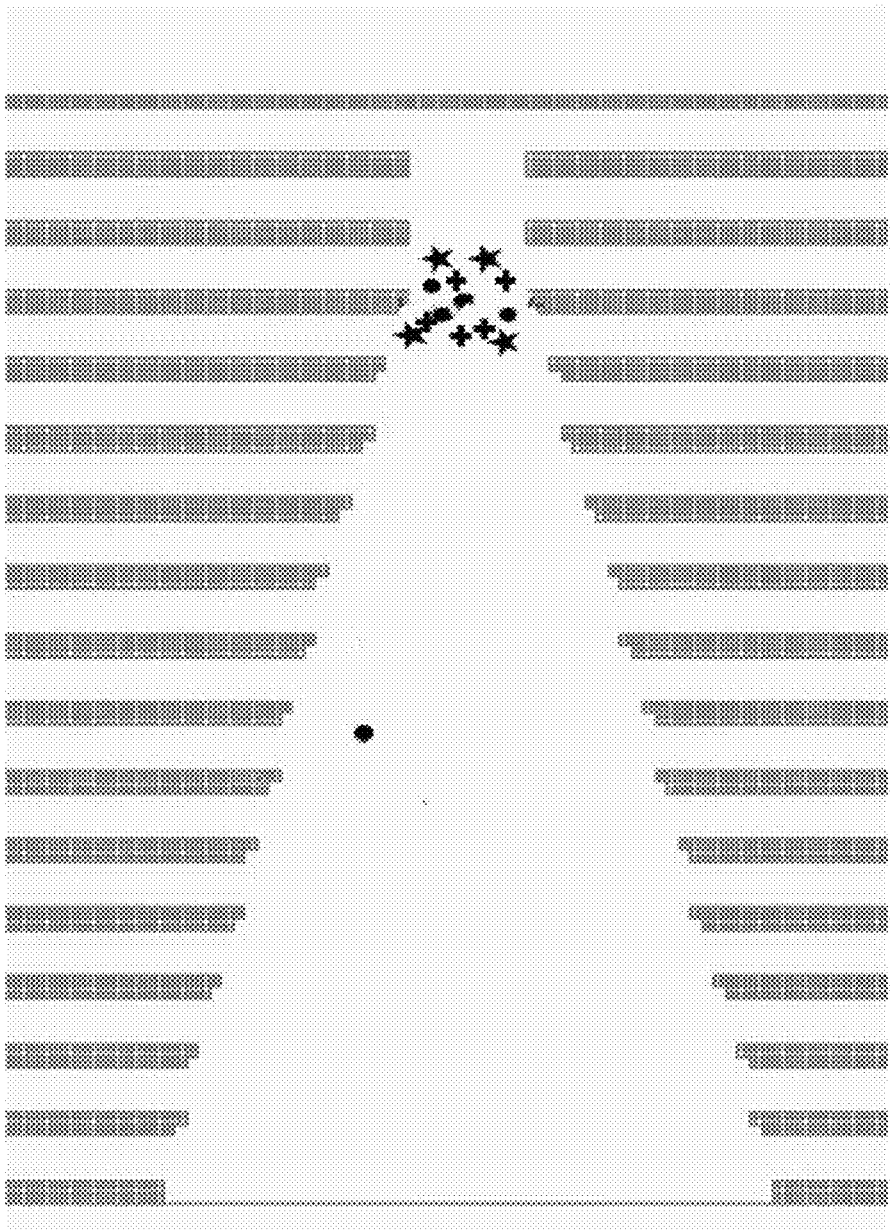
FIG. 23A is an illustration of a Simion simulation of the accumulation of ions in the accumulation region.

FIG. 23A is an illustration of a Simion simulation of the accumulation of ions in the accumulation region 17. The wide vertical lines represent the ring electrodes 22 in the ion accumulation region 17. This figure shows an alternative design for the exit end of the accumulation region 17, identical to that shown in FIG. 22A. The dots, stars and crosses represent the location in the accumulation region 17 of singly-charged ions of mass $10^4$, $10^5$ and $10^6$ Da (ten ions of each mass) at the end of a 100 ms simulation time. FIG. 23B is a table showing a summary of conditions that were used to generate the simulated trajectory. Those knowledgeable of Simion simulations will recognize the constraints imposed with the conditions listed in FIG. 23B confine the trapped ions to slightly different locations when compared to the simulation shown in FIG. 22A. This figure uses the same legend as in FIG. 21.

Figure 24A:
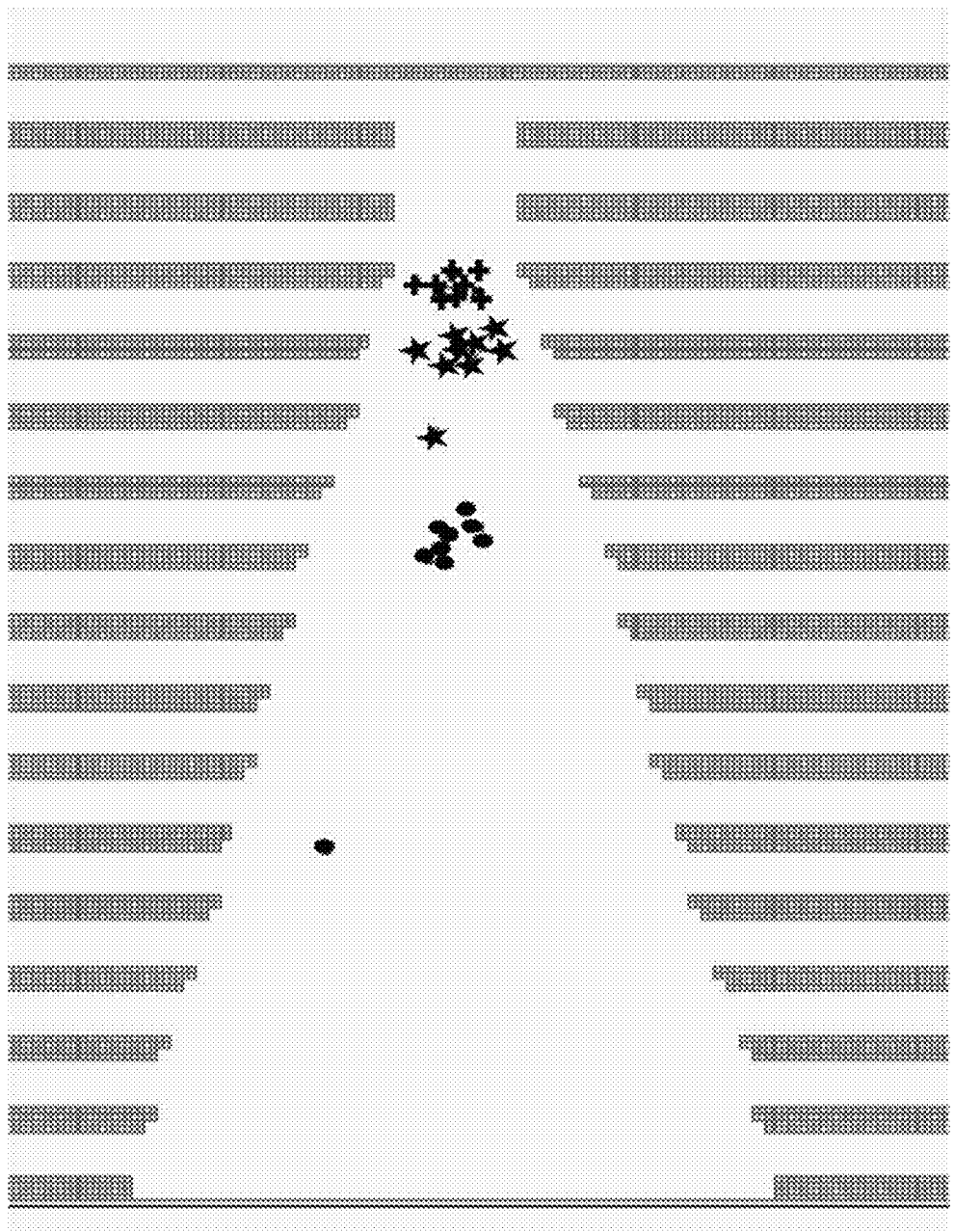
FIG. 24A is an illustration of a Simion simulation of the accumulation of ions in the accumulation region.

FIG. 24A is an illustration of a Simion simulation of the accumulation of ions in the accumulation region 17. The wide vertical lines represent the ring electrodes 22 in the ion accumulation region 17. This figure shows an alternative design for the exit end of the accumulation region 17, identical to that shown in FIG. 22A. The dots, stars and crosses represent the location in the accumulation region 17 of ten singly-charged ions of mass $10^4$, $10^5$ and $10^6$ Da (ten ions of each mass) at the end of a 100 ms simulation time. FIG. 24B is a table showing a summary of conditions that were used to generate the simulated trapped ion locations. Those knowledgeable of Simion simulations will recognize the constraints imposed with the conditions listed in FIG. 24B confine the trapped ions to slightly different locations when compared to the simulations shown in FIG. 22A and FIG. 23A. Those knowledgeable in the field will also recognize that ions smaller that $10^5$ Da or larger than $10^7$ Da can be accumulated with proper choices of gas and electric conditions. This figure uses the same legend as in FIG. 21.

FIG. 25 shows an embodiment of detector useable in the present invention. The detector is an assembly of porous metal components and an insulating fixture (flange) 100 serving as an end cap on a cylindrical tube, not shown, that surrounds the drift region. A porous metal center segment 102 (in some embodiments, having a o.d. about equal to the i.d. of drift ring electrodes) and an annular segment 104 conduct gas into or out of the drift region. The center electrode 102 collects ions after they fly through the drift region and conducts the accumulating electrical charge to the amplifier. An insulating spacer 106 allows the center segment to collect ions from a defined portion of the drift region.

Figure 26:
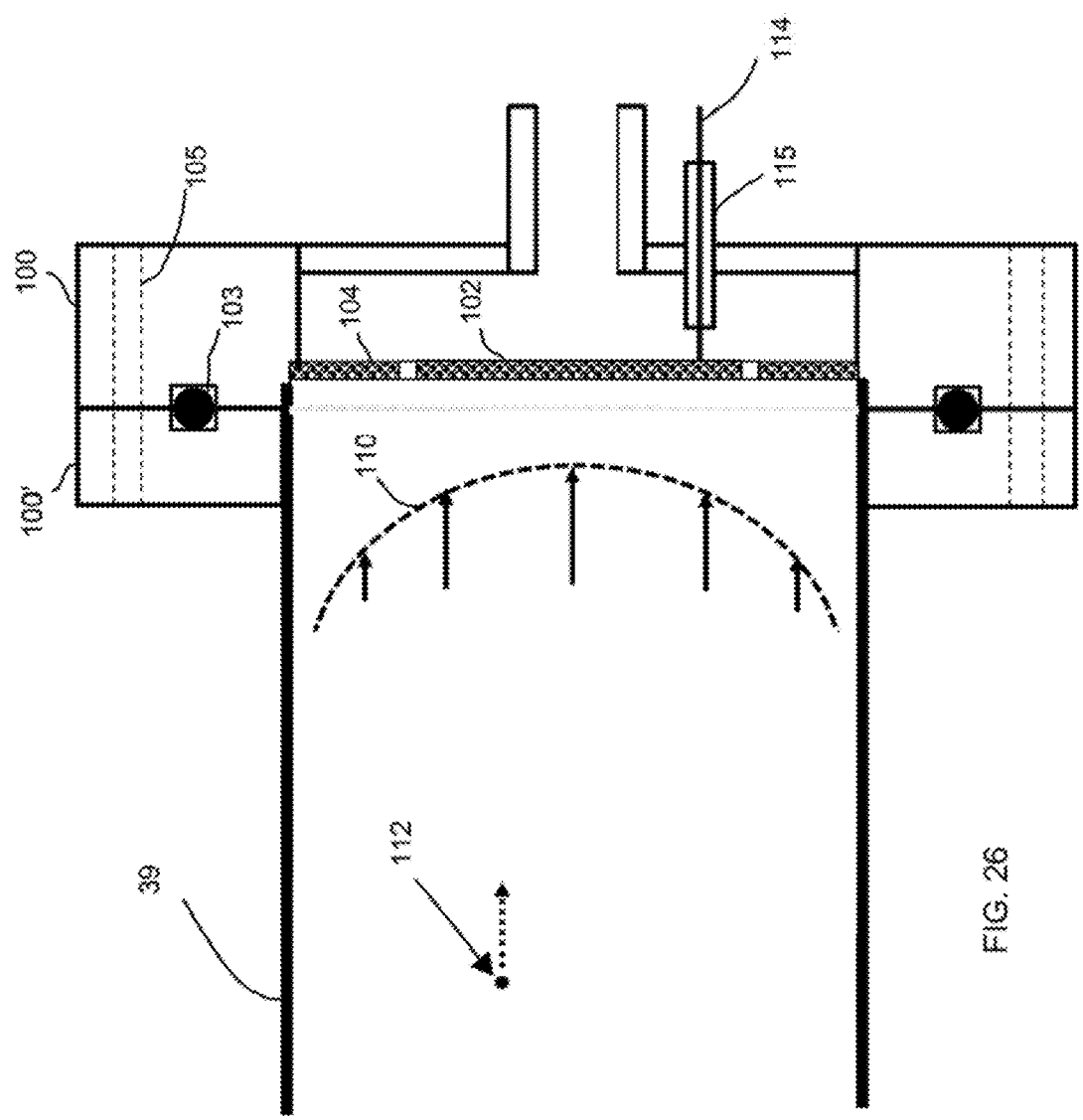
FIG. 26 is a cross-sectional figure showing a portion of a drift tube and a detector in a flange.

FIG. 26 is a cross-sectional figure showing a portion of drift tube 17 having a mating flange 100' to which flange 100 is connected. Flange 100' is fixedly attached to the end of the drift tube 39. The figure shows an o-ring 103 between the flanges. A through-hole 105 is provided for passage of a bolt which can be used to connect the two flanges together. The means for attaching the porous detector to the end of the drift tube are examples only. Based on this disclosure, those skilled in the art will recognize other ways of attaching the detector to the end of the draft tube. The figure illustrates a parabolic velocity profile 110 for gas flowing toward the detector. Gas velocity is greatest near the center of the drift tube due to drag at the drift tube wall. The dot 112 is an ion and the nearby dashed line indicates that the ion is flowing in the same direction as the gas. An electrical connection 114 surrounded by a dielectric insulator 115 passes through a wall of the flange 100. The electrical connection is in electrical contact with the center portion 102 of the detector. FIG. 27 shows the system of FIG. 26 except that the center portion 102' is curved to more nearly match the parabolic velocity profile 110. FIG. 28 shows the system of FIG. 26 in which gas is directed away from the detector assembly and has a parabolic velocity profile 120. FIG. 29 shows the system of FIG. 28 except that detector has a center portion 102" that is curved to more nearly match the parabolic velocity profile 120.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated.

I claim:

1. An apparatus, comprising:
a chamber having a conductive inner wall;
means for providing a first voltage to said inner wall;
a source of gas-borne atmospheric pressure ions;
a region into which said source directly injects said ions;
a first nozzle that is completely electrically grounded and has a first end and a second end wherein said first nozzle is non-insulated and is electrically conductive from said first end to said second end, wherein said first nozzle is configured to direct said gas-borne atmospheric pressure ions from said source into said chamber, wherein said first end of said first nozzle is connected to said region and wherein said second end of said first nozzle is located within said chamber;
a vacuum pump operatively connected to reduce the pressure within said chamber to a pressure that is sufficiently low to provide flow conditions of said gas-borne atmospheric pressure ions at said first nozzle to form an ion-laden jet of gas in said chamber; and
a second nozzle positioned in said chamber to control said ion-laden jet of gas.

2. The apparatus of claim wherein said voltage source can provide a voltage to said inner wall that is sufficient to provide a potential hill onto which said ions can be lifted by the force of said ion-laden jet of gas.

3. The apparatus of claim 1, wherein the force of said ion-laden jet of gas pushes the ions of said ion-laden jet of gas up through a potential barrier which is produced by the electrified wall of the chamber, where they rise to a potential plateau prior to entry to an ion accumulation region.

4. The apparatus of claim 1, wherein said voltage source is configured to provide a voltage within a range from 100 volts to 50 kV to said inner wall.

5. The apparatus of claim 1, wherein said second nozzle is operatively located within said chamber to control the velocity of said ion-laden jet of gas.

6. The apparatus of claim 5, wherein said second nozzle has a cylindrical restriction.

7. The apparatus of claim 5, further comprising means for adjusting the position and diameter of said second nozzle.

8. The apparatus of claim 1, wherein said source of gas-borne atmospheric pressure ions is selected from the group consisting of an electrospray source, a nebulizer, a flame, a combustion engine and a gas-phase chemical reactor.

9. The apparatus of claim 1, wherein said first nozzle comprises an orifice having a diameter in the range of about 10 to about 1000 microns or from about 200 to about 600 microns.

10. The apparatus of claim 1, wherein said vacuum pump is configured to provide a pressure in said chamber that is less than atmosphere.

11. The apparatus of claim wherein said first nozzle protrudes past said inner wall and into said chamber.

12. The apparatus of claim 1, wherein said first voltage comprises a positive potential and produces a positive polarity potential valley.

13. The apparatus of claim 1, wherein said chamber has a first output opening that is not coaxial with said first nozzle, said apparatus further comprising at least one mesh en that is within said chamber and is coaxial with said first nozzle the apparatus further comprising means for providing a second voltage to said screen sufficient to deflect ions within said jet toward said first output opening.

14. The apparatus of claim 13, wherein said screen has a transmission of the gas of said gas-borne atmospheric pressure ions within a range of 75-98%.

15. The apparatus of claim 13, wherein said screen comprises a shape selected from the group consisting of flat, parabolic, hyperbolic and spherical shaped for the purpose of steering ions more effectively into an ion accumulation region.

16. A method, comprising:
providing the apparatus of claim 1;
applying a first voltage to said conductive inner wall; and directing said gas-borne atmospheric pressure ions from said source into said chamber to form said ion-laden jet of gas in said chamber.

17. The method of claim 16, wherein said first voltage is sufficient to provide a potential hill onto which said ions can be lifted by the force of said ion-laden jet of gas.

18. The method of claim 16, wherein the force of said ion-laden jet of gas pushes the ions of said ion-laden jet of gas up through a potential barrier which is produced by the electrified wall of said chamber, where they rise to a potential plateau prior to entry to an ion accumulation region.

19. The method of claim 16, wherein said first voltage is within a range from 100 volts to 50 kV to said inner wall.

20. The method of claim 16, further comprising using said second nozzle to reduce the velocity of said ion-laden jet of gas.

21. The method of claim 16, comprising providing a pressure in said chamber that is less than atmosphere.

22. The method of claim 16, wherein said first voltage comprises positive potential and produces a positive polarity potential valley.

23. The method of claim 16, wherein said chamber has a first output opening that is not coaxial with said first nozzle, said apparatus further comprising at least one mesh screen that is within said chamber and is coaxial with said first nozzle, the method further comprising providing a second voltage to said screen sufficient to deflect ions within said jet toward said first output opening.

24. The method of claim 23, wherein said screen has a transmission of the gas of said gas-borne atmospheric pressure ions within a range of 75-98%.

25. The method of claim 16, further comprising means for shutting off said flow conditions.

* * * * *